(12) United States Patent
Suematsu et al.

(10) Patent No.: US 10,582,877 B2
(45) Date of Patent: Mar. 10, 2020

(54) HIGH-FREQUENCY DEVICE

(71) Applicant: Sharp Kabushiki Kaisha, Sakai, Osaka (JP)

(72) Inventors: Eiji Suematsu, Sakai (JP); Keisuke Satoh, Sakai (JP); Itaru Hogyoku, Sakai (JP)

(73) Assignee: Sharp Kabushiki Kaisha, Sakai (JP)

( * ) Notice: Subject to any disclaimer, the term of this patent is extended or adjusted under 35 U.S.C. 154(b) by 445 days.

(21) Appl. No.: 15/516,713

(22) PCT Filed: Sep. 30, 2015

(86) PCT No.: PCT/JP2015/077834
§ 371 (c)(1),
(2) Date: Apr. 4, 2017

(87) PCT Pub. No.: WO2016/084473
PCT Pub. Date: Jun. 2, 2016

(65) Prior Publication Data
US 2017/0311840 A1 Nov. 2, 2017

(30) Foreign Application Priority Data

Nov. 28, 2014 (JP) ................................ 2014-242161

(51) Int. Cl.
*A61B 5/05* (2006.01)
*A61B 5/0205* (2006.01)
(Continued)

(52) U.S. Cl.
CPC .......... *A61B 5/0507* (2013.01); *A61B 5/0205* (2013.01); *A61B 5/02405* (2013.01);
(Continued)

(58) Field of Classification Search
CPC . A61B 5/0507; A61B 5/0816; A61B 5/02444; A61B 5/02405; A61B 5/7246
See application file for complete search history.

(56) References Cited

U.S. PATENT DOCUMENTS

2009/0203972 A1* 8/2009 Heneghan ............ A61B 5/0507
600/301
2010/0130873 A1* 5/2010 Yuen .................... A61B 5/0205
600/484
(Continued)

FOREIGN PATENT DOCUMENTS

| JP | 2010-120493 A | 6/2010 |
|----|---------------|--------|
| JP | 2014-176427 A | 9/2014 |
| JP | 2014-215200 A | 11/2014 |

OTHER PUBLICATIONS

Official Communication issued in International Patent Application No. PCT/JP2015/077834, dated Dec. 28, 2015.

*Primary Examiner* — Sean P Dougherty
(74) *Attorney, Agent, or Firm* — Keating & Bennett, LLP

(57) ABSTRACT

A high-frequency device that detects biological information related to heartbeat, respiration, and the like with high accuracy. A high-frequency device (1) includes a biological signal extracting unit (heartbeat signal extracting unit 53, respiration signal extracting unit 63) that extracts a biological signal representing a specific frequency component; and an autocorrelation function processing unit (heartbeat autocorrelation function processing unit 54, respiratory autocorrelation function processing unit 64) that determines periodicity of an autocorrelation function to calculate biological information.

4 Claims, 14 Drawing Sheets

(51) Int. Cl.
*A61B 5/00* (2006.01)
*A61B 5/024* (2006.01)
*A61B 5/08* (2006.01)

(52) U.S. Cl.
CPC ...... *A61B 5/02438* (2013.01); *A61B 5/02444* (2013.01); *A61B 5/0816* (2013.01); *A61B 5/7207* (2013.01); *A61B 5/7225* (2013.01); *A61B 5/7246* (2013.01)

(56) References Cited

U.S. PATENT DOCUMENTS

| | | | |
|---|---|---|---|
| 2010/0152600 A1* | 6/2010 | Droitcour | A61B 5/05 600/534 |
| 2010/0198083 A1* | 8/2010 | Lin | A61B 5/05 600/484 |
| 2010/0241010 A1* | 9/2010 | Lin | A61B 5/05 600/484 |
| 2011/0257536 A1* | 10/2011 | Ser | A61B 5/0205 600/484 |
| 2013/0053653 A1* | 2/2013 | Cuddihy | A61B 5/0205 600/301 |
| 2016/0030006 A1 | 2/2016 | Okuya et al. | |

\* cited by examiner 1, 2: HIGH-FREQUENCY DEVICE
5a: RADIO WAVE RADAR UNIT
10: LIVING BODY
11: TRANSMISSION SIGNAL
12: REFLECTION SIGNAL
21: OSCILLATOR
22: AMPLIFIER
22s: ANALOG SIGNAL
25: TRANSMISSION ANTENNA
30: RECEPTION ANTENNA
31: LOW-NOISE AMPLIFIER
31s: ANALOG SIGNAL
32: MIXER
33: FILTER
33s: ANALOG SIGNAL THAT HAS RECEIVED DOPPLER SHIFT
90: DISPLAY
400, 401: SIGNAL PROCESSING CIRCUIT 40a: DIGITAL SIGNAL GENERATING UNIT
41: INPUT TERMINAL
43: HIGH-PASS FILTER
44: LOW-PASS FILTER
45: AMPLIFIER
46: AD CONVERTER
46s: DIGITAL SIGNAL
90: DISPLAY
400: SIGNAL PROCESSING CIRCUIT
500: DIGITAL SIGNAL PROCESSING UNIT (DSP)

FIG. 4

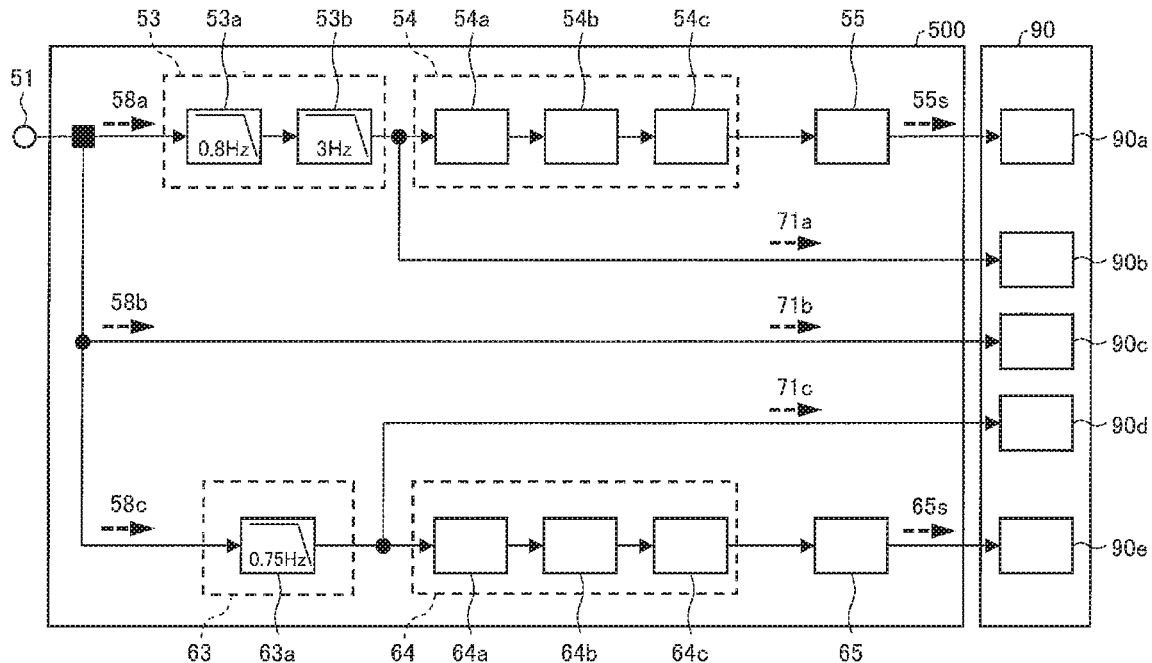

51: INPUT TERMINAL
53: HEARTBEAT SIGNAL EXTRACTING UNIT
53a: HIGH-PASS FILTER
53b: LOW-PASS FILTER
54: SAMPLING PROCESSING UNIT
54a: SAMPLING PROCESSING UNIT
54b: HEARTBEAT AUTOCORRELATION FUNCTION CALCULATING UNIT
54c: PEAK DETECTING UNIT
55: NUMBER-OF-BEATS-OF-HEART DETERMINING UNIT
55s: NUMBER-OF-BEATS-OF-HEART SIGNAL
58s: FIRST DIGITAL SIGNAL
58b: SECOND DIGITAL SIGNAL
58c: THIRD DIGITAL SIGNAL
63: RESPIRATORY SIGNAL EXTRACTING UNIT
63a: LOW-PASS FILTER
64: RESPIRATORY AUTOCORRELATION FUNCTION PROCESSING UNIT
64a: SAMPLING PROCESSING UNIT
64b: RESPIRATORY AUTOCORRELATION FUNCTION CALCULATING UNIT
64c: PEAK DETECTING UNIT
65: NUMBER-OF-RESPIRATIONS DETERMINING UNIT
65s: NUMBER-OF-RESPIRATIONS SIGNAL
71a: HEARTBEAT WAVEFORM SIGNAL
71b: BODY MOVEMENT WAVEFORM SIGNAL
71c: RESPIRATORY WAVEFORM SIGNAL
90: DISPLAY
90a: NUMBER-OF-BEATS-OF-HEART DISPLAYING UNIT
90b: HEARTBEAT WAVEFORM DISPLAYING UNIT
90c: BODY MOVEMENT WAVEFORM DISPLAYING UNIT
90d: RESPIRATORY WAVEFORM DISPLAYING UNIT
90e: NUMBER-OF-RESPIRATIONS DISPLAYING UNIT
500: DIGITAL SIGNAL PROCESSING UNIT (DSP)

40b: DIGITAL SIGNAL GENERATING UNIT
41: INPUT TERMINAL
43a, 43b: HIGH-PASS FILTER
44a, 44b: LOW-PASS FILTER
45a, 45b: AMPLIFIER
46a, 46b: AD CONVERTER
46sa: FIRST BIOLOGICAL DIGITAL SIGNAL
46sb: SECOND BIOLOGICAL DIGITAL SIGNAL
48: TERMINAL
48a: FIRST ANALOG SIGNAL
48b: SECOND ANALOG SIGNAL
90: DISPLAY
401: SIGNAL PROCESSING CIRCUIT
501: DIGITAL SIGNAL PROCESSING UNIT (DSP)

FIG. 6

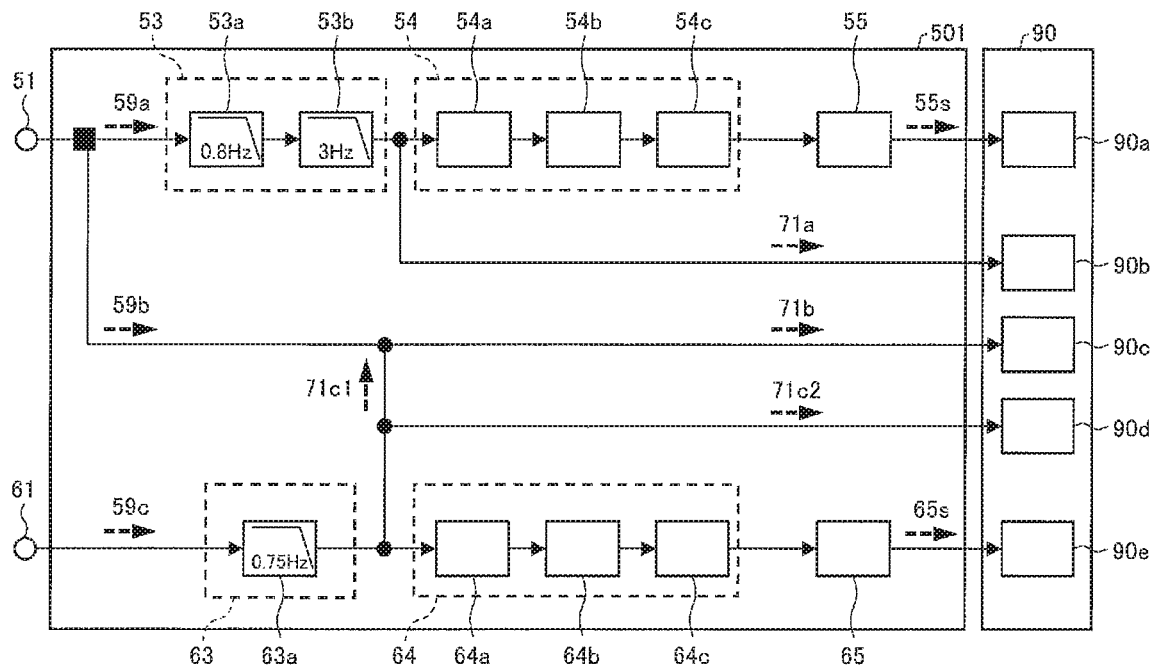

51, 61: INPUT TERMINAL
53: HEARTBEAT SIGNAL EXTRACTING UNIT
53a: HIGH-PASS FILTER
53b: LOW-PASS FILTER
54: SAMPLING PROCESSING UNIT
54a: SAMPLING PROCESSING UNIT
54b: HEARTBEAT AUTOCORRELATION FUNCTION CALCULATING UNIT
54c: PEAK DETECTING UNIT
55: NUMBER-OF-BEATS-OF-HEART DETERMINING UNIT
55s: NUMBER-OF-BEATS-OF-HEART SIGNAL
59a: HEARTBEAT DIGITAL SIGNAL
59b: BODY MOVEMENT DIGITAL SIGNAL
59c: RESPIRATORY DIGITAL SIGNAL
63: RESPIRATORY SIGNAL EXTRACTING UNIT
63a: LOW-PASS FILTER
64: RESPIRATORY AUTOCORRELATION FUNCTION PROCESSING UNIT

64a: SAMPLING PROCESSING UNIT
64b: RESPIRATORY AUTOCORRELATION FUNCTION CALCULATING UNIT
64c: PEAK DETECTING UNIT
65: NUMBER-OF-RESPIRATIONS DETERMINING UNIT
65s: NUMBER-OF-RESPIRATIONS SIGNAL
71a: HEARTBEAT WAVEFORM SIGNAL
71b: BODY MOVEMENT WAVEFORM SIGNAL
71c1, 72c2: RESPIRATORY WAVEFORM SIGNAL
90: DISPLAY
90a: NUMBER-OF-BEATS-OF-HEART DISPLAYING UNIT
90b: HEARTBEAT WAVEFORM DISPLAYING UNIT
90c: BODY MOVEMENT WAVEFORM DISPLAYING UNIT
90d: RESPIRATORY WAVEFORM DISPLAYING UNIT
90e: NUMBER-OF-RESPIRATIONS DISPLAYING UNIT
501: DIGITAL SIGNAL PROCESSING UNIT (DSP)

FIG. 7

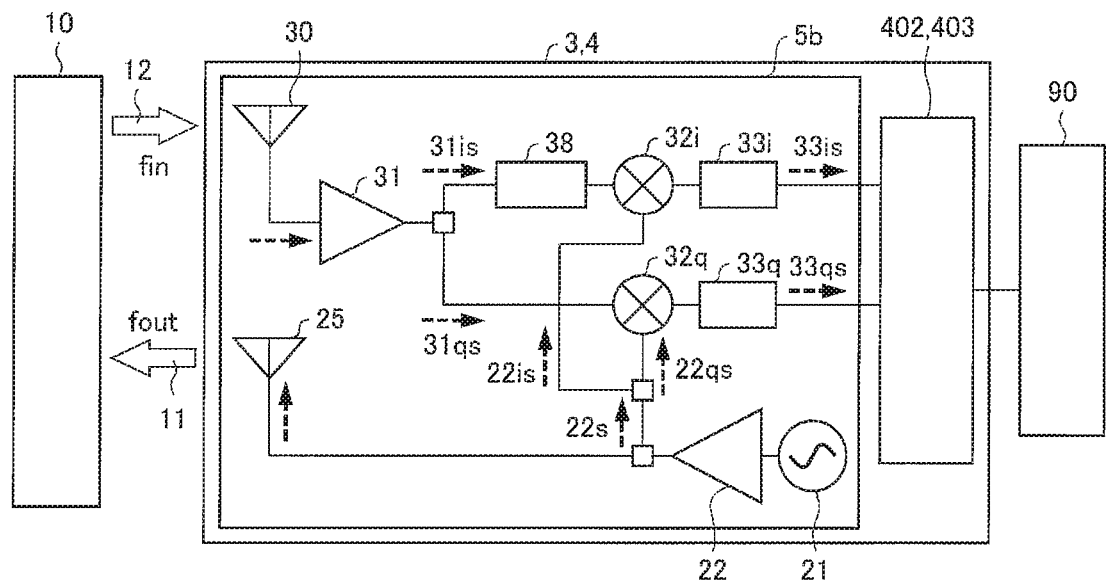

3, 4: HIGH-FREQUENCY DEVICE
5b: RADIO WAVE RADAR UNIT
10: LIVING BODY
11: TRANSMISSION SIGNAL
12: REFLECTION SIGNAL
21: OSCILLATOR
22: AMPLIFIER
22is: I LOCAL OSCILLATION SIGNAL
22qs: Q LOCAL OSCILLATION SIGNAL
22s: ANALOG SIGNAL
25: TRANSMISSION ANTENNA
30: RECEPTION ANTENNA
31: LOW-NOISE AMPLIFIER
31is: I ANALOG SIGNAL
31qs: Q ANALOG SIGNAL
32i: I MIXER
32q: Q MIXER
33i, 33q: FILTER
33is: I BASEBAND SIGNAL
33qs: Q BASEBAND SIGNAL
38: PHASE SHIFTER
90: DISPLAY
402, 403: SIGNAL PROCESSING CIRCUIT

40ci FIRST DIGITAL SIGNAL GENERATING UNIT
40Cq: SECOND DIGITAL SIGNAL GENERATING UNIT
41i, 41q: INPUT TERMINAL
43: HIGH-PASS FILTER
44: LOW-PASS FILTER
45: AMPLIFIER
46: AD CONVERTER
46si: I DIGITAL SIGNAL
46sq: Q DIGITAL SIGNAL
90: DISPLAY
402: SIGNAL PROCESSING CIRCUIT
502: DIGITAL SIGNAL PROCESSING UNIT (DSP)

FIG. 9

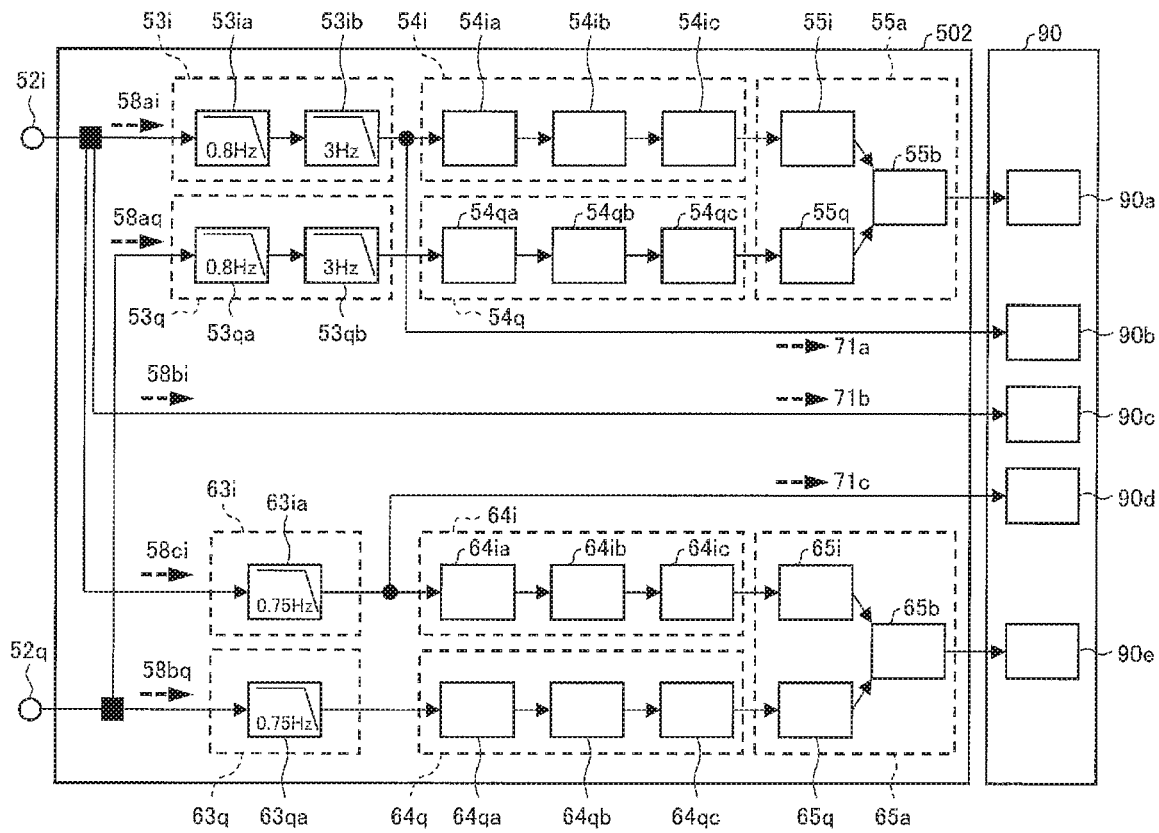

52i, 52q: INPUT TERMINAL
53i: FIRST HEARTBEAT SIGNAL EXTRACTING UNIT
53ia, 53qa: HIGH-PASS FILTER
53ib, 53qb: LOW-PASS FILTER
53q: SECOND HEARTBEAT SIGNAL EXTRACTING UNIT
54i: FIRST HEARTBEAT AUTOCORRELATION FUNCTION PROCESSING UNIT
54ia, 54qa: SAMPLING PROCESSING UNIT
54ib: FIRST HEARTBEAT AUTOCORRELATION FUNCTION CALCULATING UNIT
54ic, 54qc: PEAK DETECTING UNIT
54q: SECOND HEARTBEAT AUTOCORRELATION FUNCTION PROCESSING UNIT
54qb: SECOND HEARTBEAT AUTOCORRELATION FUNCTION CALCULATING UNIT
55a: NUMBER-OF-BEATS-OF-HEART DETERMINING UNIT
55b: DISPLAY NUMBER-OF-BEATS-OF-HEART DETERMINING UNIT
55i: FIRST NUMBER-OF-BEATS-OF-HEART DETERMINING UNIT
55q: SECOND NUMBER-OF-BEATS-OF-HEART DETERMINING UNIT
58ai: FIRST I DIGITAL SIGNAL
58bi: SECOND I DIGITAL SIGNAL
58ci: THIRD I DIGITAL SIGNAL
58aq: FIRST Q DIGITAL SIGNAL
58bq: SECOND Q DIGITAL SIGNAL
63i: FIRST NUMBER-OF-RESPIRATIONS EXTRACTING UNIT
63ia, 63qa: LOW-PASS FILTER

63q: SECOND NUMBER-OF-RESPIRATIONS EXTRACTING UNIT
64i: FIRST RESPIRATORY AUTOCORRELATION FUNCTION PROCESSING UNIT
64ia, 64qa: SAMPLING PROCESSING UNIT
64ib: RESPIRATORY AUTOCORRELATION FUNCTION CALCULATING UNIT
64ic, 64qc: PEAK DETECTING UNIT
64q: SECOND RESPIRATORY AUTOCORRELATION FUNCTION PROCESSING UNIT
64qb: SECOND RESPIRATORY AUTOCORRELATION FUNCTION CALCULATING UNIT
65a: NUMBER-OF-RESPIRATIONS DETERMINING UNIT
65b: DISPLAY NUMBER-OF-RESPIRATIONS DETERMINING UNIT
65i: FIRST NUMBER-OF-RESPIRATIONS DETERMINING UNIT
65q: SECOND NUMBER-OF-RESPIRATIONS DETERMINING UNIT
71a: HEARTBEAT WAVEFORM SIGNAL
71b: BODY MOVEMENT WAVEFORM SIGNAL
71c: RESPIRATORY WAVEFORM SIGNAL
90: DISPLAY
90a: NUMBER-OF-BEATS-OF-HEART DISPLAYING UNIT
90b: HEARTBEAT WAVEFORM DISPLAYING UNIT
90c: BODY MOVEMENT WAVEFORM DISPLAYING UNIT
90d: RESPIRATORY WAVEFORM DISPLAYING UNIT
90e: NUMBER-OF-RESPIRATIONS DISPLAYING UNIT
502: DIGITAL SIGNAL PROCESSING UNIT (DSP)

FIG. 11

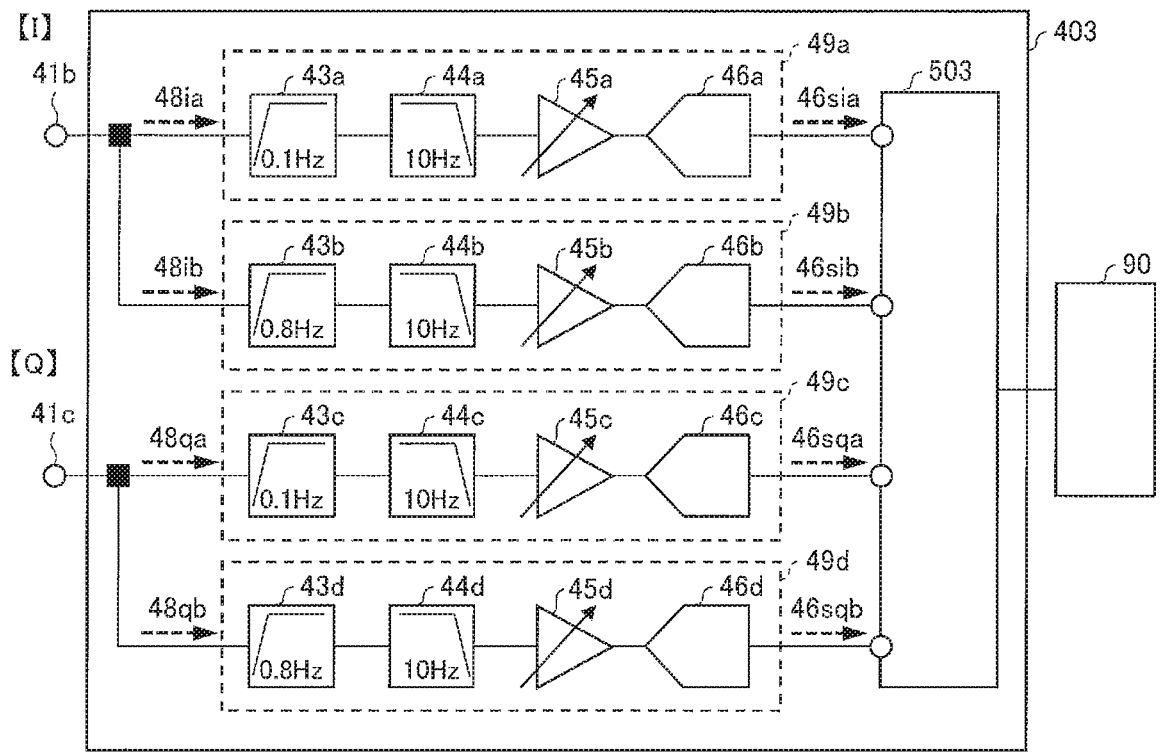

41b, 41c: INPUT TERMINAL
43a, 43b, 43c, 43d: HIGH-PASS FILTER
44a, 44b, 44c, 44d: LOW-PASS FILTER
45a, 45b, 45c, 45d: AMPLIFIER
46a, 46b, 46c, 46d: AD CONVERTER
46sia: I HEARTBEAT DIGITAL SIGNAL
46sib: I RESPIRATORY DIGITAL SIGNAL
46sqa: Q HEARTBEAT DIGITAL SIGNAL
46sqb: Q RESPIRATORY DIGITAL SIGNAL
48ia: I HEARTBEAT ANALOG SIGNAL
48ib: I RESPIRATORY ANALOG SIGNAL
48qa: Q HEARTBEAT ANALOG SIGNAL
48qb: Q RESPIRATORY ANALOG SIGNAL
49a: I HEARTBEAT DIGITAL SIGNAL GENERATING UNIT
49b: I RESPIRATORY DIGITAL SIGNAL GENERATING UNIT
49c: Q HEARTBEAT DIGITAL SIGNAL GENERATING UNIT
49d: Q RESPIRATORY DIGITAL SIGNAL GENERATING UNIT
90: DISPLAY
403: SIGNAL PROCESSING CIRCUIT
503: DIGITAL SIGNAL PROCESSING UNIT (DSP)

FIG. 12

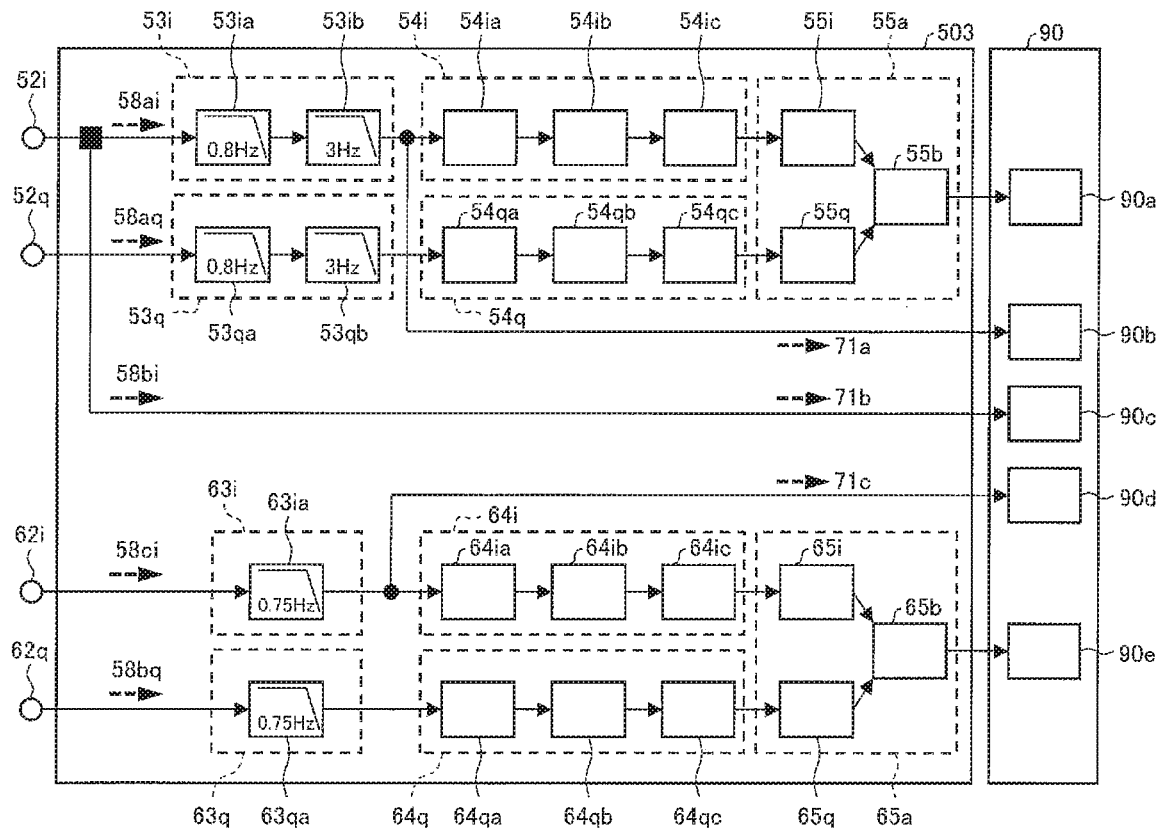

52i, 52q, 62i, 62q: INPUT TERMINAL
53i: FIRST HEARTBEAT SIGNAL EXTRACTING UNIT
53ia, 53qa: HIGH-PASS FILTER
53ib, 53qb: LOW-PASS FILTER
53q: SECOND HEARTBEAT SIGNAL EXTRACTING UNIT
54i: FIRST HEARTBEAT AUTOCORRELATION FUNCTION PROCESSING UNIT
54ia, 54qa: SAMPLING PROCESSING UNIT
54ib: FIRST HEARTBEAT AUTOCORRELATION FUNCTION CALCULATING UNIT
54ic, 54qc: PEAK DETECTING UNIT
54q: SECOND HEARTBEAT AUTOCORRELATION FUNCTION PROCESSING UNIT
54qb: SECOND HEARTBEAT AUTOCORRELATION FUNCTION CALCULATING UNIT
55a: NUMBER-OF-BEATS-OF-HEART DETERMINING UNIT
55b: DISPLAY NUMBER-OF-BEATS-OF-HEART DETERMINING UNIT
55i: FIRST NUMBER-OF-BEATS-OF-HEART DETERMINING UNIT
55q: SECOND NUMBER-OF-BEATS-OF-HEART DETERMINING UNIT
58ai: FIRST I DIGITAL SIGNAL
58bi: SECOND I DIGITAL SIGNAL
58ci: THIRD I DIGITAL SIGNAL
58aq: FIRST Q DIGITAL SIGNAL
58bq: SECOND Q DIGITAL SIGNAL
63i: FIRST NUMBER-OF-RESPIRATIONS EXTRACTING UNIT
63ia, 63qa: LOW-PASS FILTER
63q: SECOND NUMBER-OF-RESPIRATIONS EXTRACTING UNIT
64i: FIRST RESPIRATORY AUTOCORRELATION FUNCTION PROCESSING UNIT
64ia, 64qa: SAMPLING PROCESSING UNIT
64ib: RESPIRATORY AUTOCORRELATION FUNCTION CALCULATING UNIT
64ic, 64qc: PEAK DETECTING UNIT
64q: SECOND RESPIRATORY AUTOCORRELATION FUNCTION PROCESSING UNIT
64qb: SECOND RESPIRATORY AUTOCORRELATION FUNCTION CALCULATING UNIT
65a: NUMBER-OF-RESPIRATIONS DETERMINING UNIT
65b: DISPLAY NUMBER-OF-RESPIRATIONS DETERMINING UNIT
65i: FIRST NUMBER-OF-RESPIRATIONS DETERMINING UNIT
65q: SECOND NUMBER-OF-RESPIRATIONS DETERMINING UNIT
71a: HEARTBEAT WAVEFORM SIGNAL
71b: BODY MOVEMENT WAVEFORM SIGNAL
71c1, 72c2: RESPIRATORY WAVEFORM SIGNAL
90: DISPLAY
90a: NUMBER-OF-BEATS-OF-HEART DISPLAYING UNIT
90b: HEARTBEAT WAVEFORM DISPLAYING UNIT
90c: BODY MOVEMENT WAVEFORM DISPLAYING UNIT
90d: RESPIRATORY WAVEFORM DISPLAYING UNIT
90e: NUMBER-OF-RESPIRATIONS DISPLAYING UNIT
503: DIGITAL SIGNAL PROCESSING UNIT (DSP)

101: SENSOR UNIT
301: LOCAL OSCILLATOR
302: SPLITTER
303: TRANSMISSION ANTENNA
304: RECEPTION ANTENNA
305, 308: SPLITTER
306, 307: MIXER
309, 310: LOW-PASS FILTER
311, 312: AD CONVERTER
313: $B_i(t)$ SIGNAL
314: $B_q(t)$ SIGNAL

FIG. 14
Prior Art

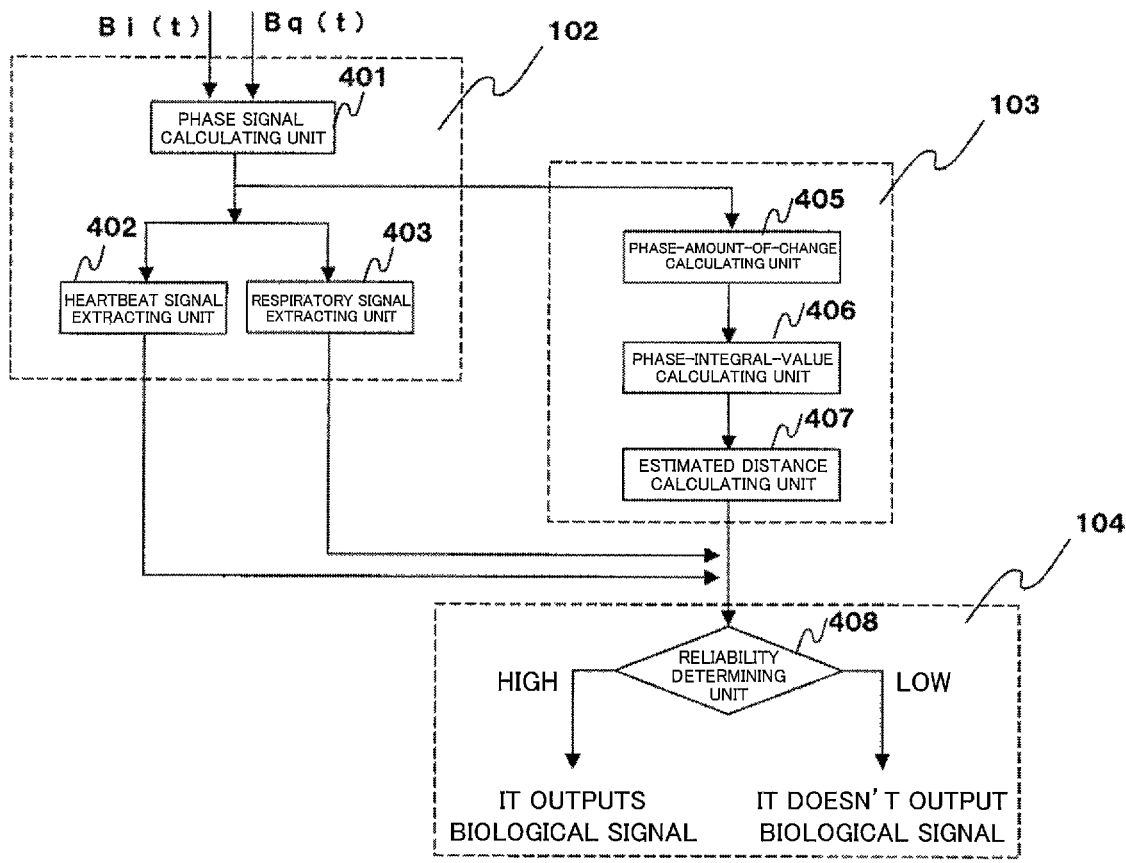

102: BIOLOGICAL SIGNAL EXTRACTING UNIT
103: DISTANCE CALCULATING UNIT
104: BIOLOGICAL SIGNAL OUTPUT DETERMINING UNIT
401: PHASE SIGNAL CALCULATING UNIT
402: HEARTBEAT SIGNAL EXTRACTING UNIT
403: RESPIRATORY SIGNAL EXTRACTING UNIT
405: PHASE-AMOUNT-OF-CHANGE CALCULATING UNIT
406: PHASE-INTEGRAL-VALUE CALCULATING UNIT
407: ESTIMATED DISTANCE CALCULATING UNIT
408: RELIABILITY DETERMINING UNIT

HIGH-FREQUENCY DEVICE

TECHNICAL FIELD

The present invention relates to a high-frequency device for sensing biological information such as the number of beats of the heart.

BACKGROUND ART

There has been widely known a technique for obtaining the vibration state and displacement of a measurement target by irradiating the measurement target with electromagnetic waves and using a Doppler shift of reflected waves that are reflected on the measurement target. Since electromagnetic waves in the microwave to millimeter wave bands have a characteristic of passing through a medium such as a dielectric, attempts by using such electromagnetic waves have been proposed in recent years to detect beating of the heart and respiration that appear as vibrations in the body of a human (examinee) by irradiating the examinee with microwaves. With the use of microwaves, the examinee can be subjected to measurement without touching the body and with clothes on, thereby reducing the burden imposed on the examinee during sensing. An example of such a sensing device using microwaves is a biological signal detecting device disclosed in PTL 1.

The above biological signal detecting device will be described with reference to FIGS. 13 and 14. The biological signal detecting device includes a sensor unit 101, a biological signal extracting unit 102, a distance calculating unit 103, and a biological signal output determining unit 104.

FIG. 13 schematically illustrates the configuration of the sensor unit 101. As illustrated in FIG. 13, a signal transmitted from a local oscillator 301 is split into two signals by a splitter 302. One of the signals is transmitted to a transmission antenna 303, and the other of the signals is further split into two signals by a splitter 308, and the split signals are input to mixers 306 and 307. The two signals obtained by the splitting by the splitter 308 have phases that are different from each other by 90 degrees.

On the other hand, the signal emitted from the transmission antenna 303 is directed toward an occupant and is mainly reflected on the surface of the body of the occupant. Then, the reflection signal that is reflected on the surface of the body is input to a reception antenna 304. At this time, since the surface of the body vibrates due to the movement (including respiration and beating of the heart) of the body of the occupant, the signal transmitted to the occupant receives a Doppler shift. Accordingly, the reflection signal is input to the reception antenna 304 as a reception signal in the state where the phase of the frequency has been modulated.

The reception signal input to the reception antenna 304 is split into two signals by a splitter 305, and the two signals are respectively input to the mixers 306 and 307. The signals input by the splitter 308 are also input to the mixers 306 and 307. The mixers 306 and 307 perform multiplication processing, and baseband signals that have received a Doppler shift are output through low-pass filters 309 and 310. The baseband signals are further subjected to analog-to-digital conversion performed by analog-to-digital (AD) converters 311 and 312 and output as Bi(t) signal and Bq(t) signal. Bi(t) signal and Bq(t) signal are signals having phases that are shifted 90 degrees at an instant.

Bi(t) signal and Bq(t) signal are input to the biological signal extracting unit 102 as illustrated in FIG. 14. The biological signal extracting unit 102 extracts a biological signal, and the distance calculating unit 103 calculates an estimated distance between the sensor unit 101 and the occupant. On the basis of the estimated distance, the biological signal output determining unit 104 sets a threshold and determines whether or not to output the biological signal. Specifically, if a reliability determining unit 408 in the biological signal output determining unit 104 determines that the distance to the occupant is constant or lower than the threshold, the biological signal is output.

Here, Bi(t) signal and Bq(t) signal, which have been converted into digital signals, are signals that have received a Doppler shift, that is, signals whose phases have been modulated by the Doppler frequency, and can be expressed as sine and cosine wave signals, respectively. In the biological signal extracting unit 102, processing is performed in which, after calculation has been performed by a phase signal calculating unit 401, from these two signals, temporal changes in phases, that is, temporal waveforms of heartbeat and respiration are extracted by a heartbeat signal extracting unit 402 and a respiratory signal extracting unit 403, respectively.

CITATION LIST

Patent Literature

PTL 1: Japanese Unexamined Patent Application Publication No. 2010-120493 (published on Jun. 3, 2010)

SUMMARY OF INVENTION

Technical Problem

A typical microwave sensor device of the related art is disclosed in PTL 1 and has such a mechanism that detects small movement of the examinee by using microwaves to obtain biological information such as heartbeat. Specifically, the device is designed to detect small movement on the surface of the body, such as beating of the heart of the examinee, by detecting a phase change (phase difference) of reflected waves of irradiation waves.

Note that if temporal changes in phases are to be detected directly on the basis of Bi(t) signal and Bq(t) signal, in the case where body movement (excluding beating of the heart and respiration) is dominant (e.g., the body is moving), a heartbeat signal and a respiratory signal tend to be buried in the body movement because those signals are minute. In addition, since the detection is performed in a wireless environment, those signals tend to be buried in noise components (clutter) such as extraneous reflection signals, and heartbeat and respiratory information can be extracted only by using direct waves (waves directly emitted onto the examinee and directly received as reflection waves).

For example, if the chest (or back) of the examinee who is sitting on a chair is directly irradiated with radio waves, the heartbeat and respiratory information can be acquired. However, in a situation where the examinee is lying, it has not been possible all the time to measure and monitor heartbeat and respiratory components of the examinee in a lying posture (e.g., the examinee is lying face down, on their back, or on their side, or changing their posture while lying).

In addition, since the heartbeat signal is more minute than the respiratory signal, it has been particularly difficult to extract the heartbeat component with high accuracy.

The present invention has been made in order to solve the above-described problems, and an object thereof is to provide a high-frequency device that can detect biological information representing the heartbeat, respiration, and the like of a living body wirelessly with high accuracy.

Solution to Problem

In order to solve the above-described problems, a high-frequency device according to an embodiment of the present invention includes a biological signal extracting unit that extracts, from a digital signal representing a biological phenomenon, which is movement that appears in a living body, a biological signal representing a specific frequency component of the digital signal; and an autocorrelation function processing unit that samples the biological signal extracted by the biological signal extracting unit, calculates an autocorrelation function on the basis of a predetermined number of the biological signals that are sampled, and determines periodicity of the autocorrelation function from a peak value of a correlation coefficient to calculate biological information representing the biological phenomenon.

Advantageous Effects of Invention

According to an embodiment of the present invention, even if the living body is moving or if there are many noise components such as extraneous reflection signals, it is possible to realize a high-frequency device that detects biological information representing the heartbeat, respiration, and the like with high accuracy by using autocorrelation functions.

BRIEF DESCRIPTION OF DRAWINGS

FIG. 4 is a block diagram schematically illustrating the configurations of a digital signal processing unit and a display included in the high-frequency device.

FIG. 6 is a block diagram schematically illustrating the configurations of a digital signal processing unit and a display included in the high-frequency device.

FIG. 7 is a block diagram schematically illustrating the configuration of a radio wave radar unit included in a high-frequency device according to the third and fourth embodiments of the present invention.

FIG. 9 is a block diagram schematically illustrating the configurations of a digital signal processing unit and a display included in the high-frequency device.

FIG. 11 is a block diagram schematically illustrating the configuration of a signal processing circuit included in a high-frequency device according to the fourth embodiment of the present invention.

FIG. 12 is a block diagram schematically illustrating the configurations of a digital signal processing unit and a display included in the high-frequency device.

FIG. 14 is a block diagram schematically illustrating the configuration of the microwave sensor device of the related art.

DESCRIPTION OF EMBODIMENTS

First Embodiment

Figure 1:
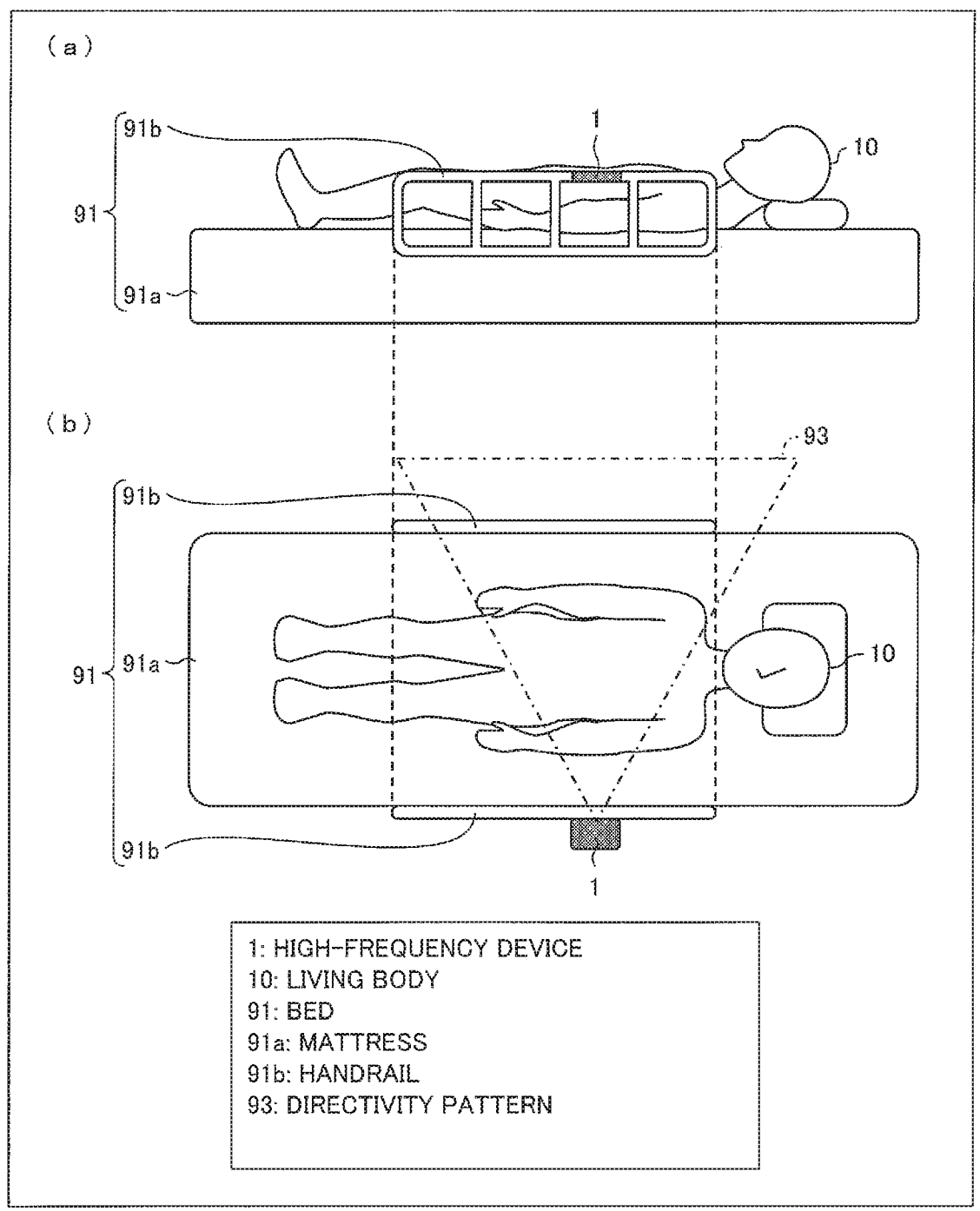
FIG. 1(a) illustrates a side view of an example of a method for using a high-frequency device according to first to fourth embodiments of the present invention.
FIG. 1(b) illustrates a top view of the example of the method for using the high-frequency device according to the first to fourth embodiments of the present invention.

An embodiment of the present invention will be described below with reference to FIGS. 1 to 4.
<Method for Using High-Frequency Device 1>
A method for using a high-frequency device 1 will be described below with reference to FIG. 1 by taking as an example the case in which the high-frequency device 1 is attached to a handrail 91b of a bed 91. FIG. 1(a) illustrates a side view of an example of the method for using the high-frequency device 1 according to this embodiment. FIG. 1(b) illustrates a top view of the example of the method for using the high-frequency device 1 according to this embodiment.

The high-frequency device 1 is a device for obtaining biological information representing a biological phenomenon of a living body 10 on the basis of a reflection signal 12 (see FIG. 2) obtained by a transmission signal 11 being reflected on the living body 10. Here, the biological phenomenon mainly means movement that appears in the upper half of the living body 10 and indicates a heartbeat component, a respiratory component, a body movement component, and the like. In addition, the body movement means the movement that appears in the upper half of the living body 10 other than beating of the heart and respiration. Furthermore, examples of the biological information include the number of beats of the heart and the number of respirations during a predetermined period, a heartbeat waveform, a respiratory waveform, a body movement waveform, and the like. The high-frequency device 1 includes a radio wave radar unit 5a and a signal processing circuit 400 (see FIG. 2).

As illustrated in FIG. 1, a directivity pattern 93 of a transmission antenna 25 (see FIG. 2) included in the radio wave radar unit 5a is adjusted in such a manner that the transmission signal 11 (see FIG. 2) emitted from the high-frequency device 1 is desirably emitted onto the upper half of the living body 10. As an example of the adjustment, the adjustment can be achieved by using the number of patches of a microstrip patch antenna. The reflection signal 12 is a reception signal of the high-frequency device 1. By adjusting the directivity pattern 93, even if the living body 10 is sleeping, the heartbeat component, the respiratory component, and the body movement component can be monitored.

In particular, by being attached to the handrail 91b of the bed 91, the high-frequency device 1 emits the transmission signal 11 toward the upper half of the living body 10 in a direction substantially parallel to a plane along which the living body 10 contacts a mattress 91a of the bed 91. Accordingly, it is possible all the time to measure and monitor the heartbeat component, the respiratory component, and the body movement component of the living body 10 in a sleeping posture (lying face down, on their back, on their side, moving while sleeping, or the like).

This is because the transmission signal 11 is emitted from a position that is relatively close to the living body 10 and because the irradiation with the transmission signal 11 is in the above-described substantially horizontal direction, and thereby there are a few reflection objects that are irradiated with the transmission signal 11 and the reflection signal 12. That is, the high-frequency device 1 receives a few extraneous reflection signals. In addition, the high-frequency device 1 processes the heartbeat signal representing the heartbeat component and the respiratory signal representing the respiratory component by using autocorrelation functions, which will be described later. The high-frequency device 1 can accordingly measure and monitor the heartbeat component and the like on the basis of an indirect reflection signal, which will be described later, also in a bedroom in which many extraneous reflection signals are present.

Note that the position for attaching the high-frequency device 1 is not limited to the handrail 91b of the bed 91 as in this embodiment. For example, the high-frequency device 1 may be attached under the bed 91 (desirably on the mattress 91a of the bed 91 at a portion opposing the plane that contacts the living body 10). Even if the high-frequency device 1 is attached in the above manner, since there are a few reflection components of the transmission signal 11 on the mattress 91a, substantially the same effects as those in the case where the high-frequency device 1 is attached as in this embodiment can be obtained.

In addition, the method for using the high-frequency device 1 in this embodiment will be applied in the same manner to high-frequency devices 2 to 4, which will be described later.

<Signal Processing Performed by Radio Wave Radar Unit 5a>

Figure 2:
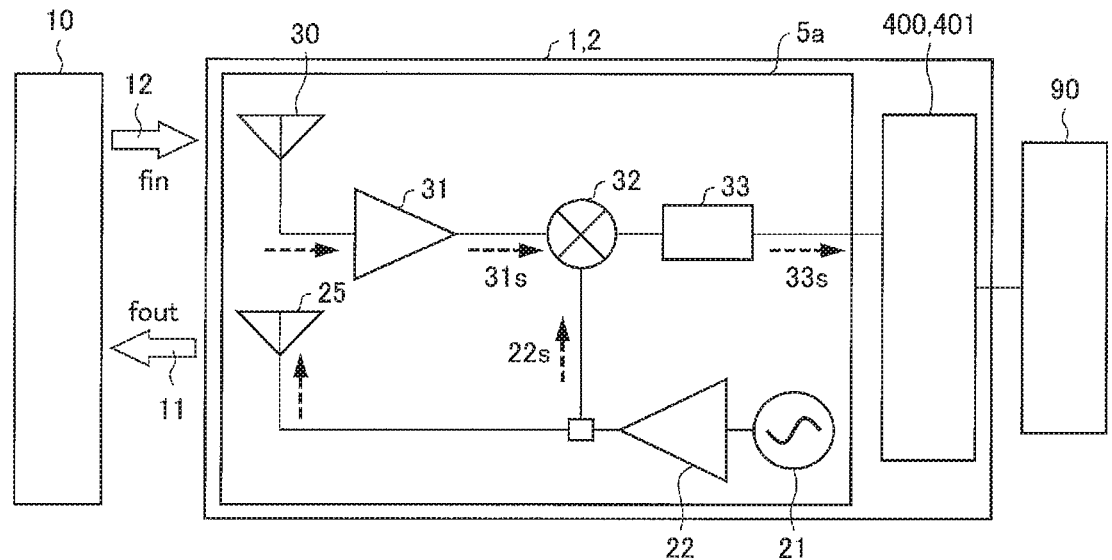
FIG. 2 is a block diagram schematically illustrating the configuration of a radio wave radar unit included in a high-frequency device according to the first and second embodiments of the present invention.

Now, signal processing performed by the radio wave radar unit 5a will be described below with reference to FIG. 2. FIG. 2 is a block diagram schematically illustrating the configuration of the radio wave radar unit 5a. The radio wave radar unit 5a emits the transmission signal 11 toward the living body 10, receives the reflection signal 12 that has been reflected on the surface of the living body 10, and generates an analog signal 33s on the basis of the reflection signal 12. As illustrated in FIG. 2, the radio wave radar unit 5a includes an oscillator 21, an amplifier 22, the transmission antenna 25, a reception antenna 30, a low-noise amplifier 31, a mixer 32, and a filter 33.

As illustrated in FIG. 2, a microwave sine wave (not illustrated) output from the oscillator 21 is amplified by the amplifier 22 and then is emitted from the transmission antenna 25 as the transmission signal 11. The emitted transmission signal 11 hits and is reflected on the surface of the living body 10, for example, on the surface of the chest part of the living body 10. At this time, the chest part of the living body 10 is moving due to beating of the heart, respiration, and body movement, and owing to this movement, a Doppler shift occurs in the transmission signal 11 that has hit the chest part. That is, the frequency of movement of the chest including beating of the heart and respiration is added to the frequency of the transmission signal 11, and accordingly, the frequency and phase of the transmission signal 11 are modulated, and the reflection signal 12 is generated. Then, the reflection signal 12 is input to the reception antenna 30.

Note that the reflection signal 12 includes both a direct reflection signal that has been emitted directly onto the living body 10 and that is directly received by the reception antenna 30 after the reflection and an indirect reflection signal that is received by the reception antenna 30 after having been reflected on an object other than the living body 10 and then reflected on the living body 10.

The reflection signal 12 input to the reception antenna 30 is amplified by the low-noise amplifier 31 and is then input to the mixer 32 as an analog signal 31s. The mixer 32 also receives an analog signal 22s that is one of two signals obtained by splitting a signal that has been transmitted from the oscillator 21 and amplified by the amplifier 22. The analog signal 31s is input to the filter 33 in the state where the frequency is down-converted by using the analog signal 22s.

The analog signal 33s output from the filter 33 becomes a baseband signal and is output as a signal that has received a Doppler shift due to the movement of the chest. That is, the analog signal 33s contains the heartbeat component, the respiratory component, and the body movement component of the living body 10. The analog signal 33s is displayed on a display 90, which will be described later, as heartbeat information, respiratory information, and body movement information after having been input to the signal processing circuit 400, which will be described later, and processed.

<Signal Processing Performed by Signal Processing Circuit 400>

Figure 3:
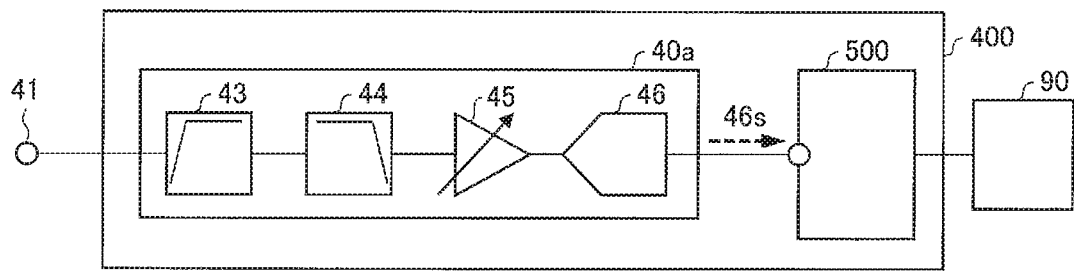
FIG. 3 is a block diagram schematically illustrating the configuration of a signal processing circuit included in a high-frequency device according to the first embodiment of the present invention.

Now, signal processing performed by the signal processing circuit 400 will be described below with reference to FIGS. 3 and 4. FIG. 3 is a block diagram schematically illustrating the configuration of the signal processing circuit 400. FIG. 4 is a block diagram schematically illustrating the configurations of a digital signal processing unit (hereinafter referred to as "DSP") 500 and the display 90, which will be described later. On the basis of the analog signal 33s that has been input, the signal processing circuit 400 calculates and determines the heartbeat information (the number of beats of the heart per minute and heartbeat waveform), the respiratory information (the number of respirations per minute and respiratory waveform), and the body movement information (body movement waveform) of the living body 10. As illustrated in FIG. 3, the signal processing circuit 400 includes a digital signal generating unit 40a and the DSP 500.

On the basis of the analog signal 33s that has been input, the digital signal generating unit 40a generates a digital signal 46s containing the heartbeat component, the respiratory component, and the body movement component of the living body 10. As illustrated in FIG. 3, the digital signal generating unit 40a includes an input terminal 41, a high-pass filter 43, a low-pass filter 44, an amplifier 45, and an AD converter 46.

On the basis of the digital signal 46s that has been input, the DSP 500 calculates and determines the above-described heartbeat information, respiratory information, and body movement information. As illustrated in FIG. 4, the DSP 500 includes an input terminal 51, a heartbeat signal extracting unit (biological signal extracting unit) 53, a heartbeat autocorrelation function processing unit (autocorrelation function processing unit) 54, a number-of-beats-of-heart determining unit 55, a respiratory signal extracting unit (biological signal extracting unit) 63, a respiratory autocorrelation function processing unit (autocorrelation function processing unit) 64, and a number-of-respirations determining unit 65.

(Signal Processing Performed by Digital Signal Generating Unit 40*a*)

As illustrated in FIG. 3, the analog signal 33*s* (see FIG. 2) is input to the input terminal 41, and then the band thereof is limited by the high-pass filter 43 (for the purpose of suppressing a direct current (dc) component) and the low-pass filter 44. As an example, the passband cutoff of the high-pass filter 43 is 0.1 Hz, and the passband cutoff of the low-pass filter 44 is 10 Hz. An analog signal in a frequency band related to heartbeat, respiration, and body movement is caused to pass through the high-pass filter 43 and the low-pass filter 44 and is then amplified by the amplifier 45.

By causing the analog signal 33*s* to pass through the high-pass filter 43 and the low-pass filter 44, for example, it is possible to suppress analog signal components other than heartbeat, respiration, and body movement in the analog signal 33*s* that has received a Doppler shift based on high-speed operation of an electric fan or the like. In addition, the amplifier 45 prevents a high-speed analog signal that has passed through the high-pass filter 43 and the low-pass filter 44 from being saturated, which may result in non-linear operation. In addition, the low-pass filter 44 functions also as an anti-aliasing filter of the AD converter 46.

The analog signal (not illustrated) output from the amplifier 45 is input to the AD converter 46 and subjected to analog-to-digital conversion. As an example, in the case where analog-to-digital conversion is performed at a sampling rate of 50 Hz at 12 bits, the passband cutoff of the low-pass filter 44 is lower than or equal to 25 Hz (10 Hz in this embodiment).

The digital signal 46*s* generated by the AD converter 46 performing analog-to-digital conversion is input to the digital signal processing unit (hereinafter referred to as "DSP") 500. The above-described heartbeat information, respiratory information, and body movement information are calculated by the DSP 500, and then these information items are displayed on the display 90.

(Signal Processing Performed by DSP 500)

As illustrated in FIG. 4, the digital signal 46*s* (see FIG. 3) input to the input terminal 51 is split into a first digital signal 58*a*, a second digital signal 58*b*, and a third digital signal 58*c*, and the three digital signals are processed concurrently.

First, the first digital signal 58*a* is input to the heartbeat signal extracting unit 53. Then, the band of the first digital signal 58*a* that has been input is limited by a high-pass filter 53*a* and a low-pass filter 53*b* included in the heartbeat signal extracting unit 53, and thereby a heartbeat signal representing heartbeat at a specific frequency is extracted.

In this embodiment, the passband cutoff frequency of the high-pass filter 53*a* is 0.8 Hz, and the passband cutoff frequency of the low-pass filter 53*b* is 3.0 Hz. Since the respiratory component is 0.2 Hz to 0.33 Hz (approximately 12 to 20 times per minute) during rest, in order to suppress the respiratory component as much as possible, the pass band cutoff frequency of the high-pass filter 53*a* is selected to be 0.8 Hz. On the other hand, since the heartbeat component is approximately 50 to 90 (0.8 Hz to 1.5 Hz in a frequency) during rest, the passband cutoff frequency of the low-pass filter 53*b* is selected to be 3.0 Hz.

The heartbeat signal extracted by the heartbeat signal extracting unit 53 is split into two signals, and one of the signals is input to the heartbeat autocorrelation function processing unit 54. Then, by the heartbeat autocorrelation function processing unit 54 performing calculation processing using an autocorrelation function, the number of beats of the heart per minute (the value of a biological phenomenon; hereinafter simply referred to as "number of beats of the heart") is calculated. The heartbeat autocorrelation function processing unit 54 includes a sampling processing unit 54*a*, a heartbeat autocorrelation function calculating unit 54*b*, and a peak detecting unit 54*c*.

In this embodiment, since the AD converter 46 performs analog-to-digital conversion at a sampling rate of 50 Hz at 12 bits, the sampling processing unit 54*a* samples the heartbeat signal from the first digital signal 58*a* 256 times in 20 ms for a sample. Upon input of the sampled heartbeat signal, the heartbeat autocorrelation function calculating unit 54*b* calculates an autocorrelation function. Then, the peak detecting unit 54*c* detects the peak value of a correlation coefficient from the autocorrelation function, and the period of the autocorrelation function is calculated. In other words, the periodicity of the autocorrelation function is determined by the peak detecting unit 54*c*. The peak detecting unit 54*c* converts the calculated period into the number of beats of the heart. Since the correlation coefficient of data obtained after 0 seconds is the largest in the autocorrelation function, the peak value of the autocorrelation coefficient excluding the data obtained after 0 seconds is detected.

In this embodiment, it takes 5 seconds for the sampling processing unit 54*a* to perform sampling processing (256 times of sampling in 20 ms for a sample), and it takes approximately 5 seconds for the heartbeat autocorrelation function calculating unit 54*b* to calculate the autocorrelation function and for the peak detecting unit 54*c* to calculate the period. Accordingly, a beat of the heart is calculated in approximately 10 seconds.

Note that details of the method for determining the periodicity related to the heartbeat component by using the autocorrelation function will be described in a third embodiment.

The number of beats of the heart calculated by the heartbeat autocorrelation function processing unit 54 is input to the number-of-beats-of-heart determining unit 55 as a signal (not illustrated) representing the number of beats of the heart. On the basis of the signal, the number-of-beats-of-heart determining unit 55 determines the number of beats of the heart to be displayed on the display 90 (specifically, a number-of-beats-of-heart displaying unit 90*a*, which will be described later) and outputs a number-of-beats-of-heart signal 55*s* representing the determined number of beats of the heart. The number-of-beats-of-heart signal 55*s* is a signal to be input to the display 90.

The determination of the number of beats of the heart by the number-of-beats-of-heart determining unit 55 is not limited to a single method. Since a signal is output approximately every 10 seconds from the heartbeat autocorrelation function processing unit 54 in this embodiment, for example, calculation for obtaining the average value, the moving average value, the median value, or the like may be performed for every three signals. In other words, any method may be used as long as a stable numerical value is output as the number of beats of the heart to be displayed on the display 90.

On the other hand, the other of the two signals split from the heartbeat signal extracted by the heartbeat signal extracting unit 53 becomes a heartbeat waveform signal 71*a* representing the change in the amplitude of heartbeat over time and is a signal to be input to the display 90. In addition, the second digital signal 58b without modification becomes a body movement waveform signal 71b representing the change in the amplitude of the body movement over time and is a signal to be input to the display 90.

Then, the third digital signal 58c is input to the respiratory signal extracting unit 63. The band of the third digital signal 58c that has been input is limited by a low-pass filter 63a included in the respiratory signal extracting unit 63, and thereby a respiratory signal representing respiration at a specific frequency is extracted.

In this embodiment, the passband cutoff frequency of the low-pass filter 63a is 0.75 Hz. This is because the respiratory signal extracting unit 63 suppresses the heartbeat component as much as possible, for the respiratory component is 0.2 Hz to 0.33 Hz (approximately 12 to 20 times per minute) during rest.

The respiratory signal extracted by the respiratory signal extracting unit 63 is split into two signals, and one of the signals is input to the respiratory autocorrelation function processing unit 64. Then, by the respiratory autocorrelation function processing unit 64 performing calculation processing using an autocorrelation function, the number of respirations per minute (the value of a biological phenomenon; hereinafter simply referred to as "number of respirations") is calculated. The respiratory autocorrelation function processing unit 64 includes a sampling processing unit 64a, a respiratory autocorrelation function calculating unit 64b, and a peak detecting unit 64c.

In this embodiment, since the AD converter 46 performs analog-to-digital conversion at a sampling rate of 50 Hz at 12 bits, the sampling processing unit 64a samples the respiratory signal from the third digital signal 58c 512 times in 20 ms for a sample. Upon input of the sampled respiratory signal, the respiratory autocorrelation function calculating unit 64b calculates an autocorrelation function. Then, the peak detecting unit 64c detects the peak value of a correlation coefficient from the autocorrelation function, and the period of the autocorrelation function is calculated. In other words, the periodicity of the autocorrelation function is determined by the peak detecting unit 64c. The peak detecting unit 64c converts the calculated period into the number of respirations.

In this embodiment, it takes 10 seconds for the sampling processing unit 64a to perform sampling processing (512 times of sampling in 20 ms for a sample), and it takes approximately 5 seconds for the respiratory autocorrelation function calculating unit 64b to calculate the autocorrelation function and for the peak detecting unit 64c to calculate the period. Accordingly, a respiration is calculated in approximately 15 seconds.

Note that details of the method for determining the periodicity related to the respiratory component by using the autocorrelation function will be described in the third embodiment.

The number of respirations calculated by the respiratory autocorrelation function processing unit 64 is input to the number-of-respirations determining unit 65 as a signal (not illustrated) representing the number of respirations. On the basis of the signal, the number-of-respirations determining unit 65 determines the number of respirations to be displayed on the display 90 (specifically, a number-of-respirations displaying unit 90e, which will be described later) and outputs a number-of-respirations signal 65s representing the determined number of respirations. The number-of-respirations signal 65s is a signal to be input to the display 90.

The determination of the number of respirations by the number-of-respirations determining unit 65 is not limited to a single method. Since a signal is output approximately every 15 seconds from the respiratory autocorrelation function processing unit 64 in this embodiment, for example, calculation for obtaining the average value, the moving average value, the median value, or the like may be performed for every three signals. In other words, any method may be used as long as a stable numerical value is output as the number of respirations to be displayed on the display 90.

On the other hand, the other of the two signals split from the respiratory signal extracted by the respiratory signal extracting unit 63 becomes a respiratory waveform signal 71c representing the change in the amplitude of respiration over time and is a signal to be input to the display 90.

<Display of Heartbeat, Respiratory, and Body Movement Information on Display 90>

Now, display of the heartbeat information, the respiratory information, and the body movement information of the living body 10 on the display 90 will be described below with reference to FIG. 4. As illustrated in FIG. 4, the display 90 includes the number-of-beats-of-heart displaying unit 90a, a heartbeat waveform displaying unit 90b, a body movement waveform displaying unit 90c, a respiratory waveform displaying unit 90d, and a number-of-respirations displaying unit 90e.

Each signal output from the DSP 500 is input to the display 90. Specifically, the number-of-beats-of-heart signal 55s is input to the number-of-beats-of-heart displaying unit 90a, the heartbeat waveform signal 71a is input to the heartbeat waveform displaying unit 90b, the body movement waveform signal 71b is input to the body movement waveform displaying unit 90c, the respiratory waveform signal 71c is input to the respiratory waveform displaying unit 90d, and the number-of-respirations signal 65s is input to the number-of-respirations displaying unit 90e. Then, the number of beats of the heart (numerical value) is displayed on the number-of-beats-of-heart displaying unit 90a, the heartbeat waveform (graph) is displayed on the heartbeat waveform displaying unit 90b, the body movement waveform (graph) is displayed on the body movement waveform displaying unit 90c, the respiratory waveform (graph) is displayed on the respiratory waveform displaying unit 90d, and the number of respirations (numerical value) is displayed on the number-of-respirations displaying unit 90e.

Examples of the display 90 include a personal computer, a cell phone, a smartphone, and the like having a display function and a data storing function. Note that the DSP 500 and the display 90 may be integrated together. For example, by wirelessly transmitting a signal that has been subjected to analog-to-digital conversion performed by the digital signal generating unit 40a and by receiving the signal by a personal computer or the like including the DSP 500 and the display 90, the personal computer or the like may process and display the signal.

<Effects>

As described above, according to this embodiment, the high-frequency device 1 extracts only a necessary band through analog filters (the high-pass filter 43 and the low-pass filter 44) and causes only the necessary band to pass through digital filters (the high-pass filter 53a and the low-pass filters 53b and 63a) too. Specifically, by extracting only the necessary band through the analog filters, excluding unnecessary signals, and by amplifying the necessary band, and then by performing analog-to-digital conversion, the high-frequency device 1 increases the dynamic range of the heartbeat or respiration band. In addition, the signal-to-noise (SN) ratios of the digital signals are increased in the digital filters. Accordingly, it is possible to increase the detection accuracy of the peak values of the correlation coefficients detected from the autocorrelation functions.

In addition, by detecting the peak values of the correlation coefficients by using the autocorrelation functions obtained by sampling the heartbeat signal and the respiratory signal, and by determining the periods of the autocorrelation functions, the high-frequency device 1 calculates the number of beats of the heart and the number of respirations. Accordingly, even if the living body 10 is moving or if there are many noise components such as extraneous reflection signals, the number of beats of the heart and the number of respirations can be calculated with high accuracy.

Typically, since the waveform of an indirect reflection signal is deformed or noise is added thereto, it is considered to be difficult to calculate biological information from the indirect reflection signal.

In this respect, according to this embodiment, it is possible to extract the heartbeat signal and the respiratory signal from the direct reflection signal and the indirect reflection signal by using the heartbeat signal extracting unit 53 and the respiratory signal extracting unit 63. Accordingly, also from the indirect reflection signal, it is possible to calculate the number of beats of the heart, the number of respirations, and the like by using the autocorrelation functions of the heartbeat signal and the respiratory signal.

In addition, if the living body is present in a relatively narrow space such as a bedroom, there are many indirect reflection signals in the space. Accordingly, even if it is not possible to capture the direct reflection signal, the high-frequency device 1 can calculate the number of beats of the heart, the number of respirations, and the like of the living body 10 present in the space by using the indirect reflection signals.

Furthermore, if the living body 10 is present in the above space, even in a situation where it is difficult to directly irradiate a desired portion of the living body 10 with the transmission signal 11, for example, when the living body 10 is lying face down, by making the transmission signal 11 reflect on a wall or the like, the portion can be indirectly irradiated with the transmission signal 11. Accordingly, by using the indirect reflection signal, it is possible to calculate the number of beats of the heart, the number of respirations, and the like regardless of the posture of the living body 10.

Second Embodiment

Another embodiment of the present invention will be described below with reference to FIGS. 5 and 6. Note that the members having the same functions as the members described in the above embodiment are denoted by the same reference numerals, and description thereof is omitted for brevity of the description.

A high-frequency device 2 according to this embodiment is different from the high-frequency device 1 according to the first embodiment in including a signal processing circuit 401 instead of the signal processing circuit 400.

<Signal Processing Performed by Signal Processing Circuit 401>

Now, signal processing performed by the signal processing circuit 401 will be described below with reference to FIGS. 5 and 6. FIG. 5 is a block diagram schematically illustrating the configuration of the signal processing circuit 401. FIG. 6 is a block diagram schematically illustrating the configurations of a DSP 501 and the display 90. As illustrated in FIG. 5, the signal processing circuit 401 includes a digital signal generating unit 40*b* and the DSP 501.

On the basis of the analog signal 33*s* (see FIG. 2) that has been input, the digital signal generating unit 40*b* generates a digital signal 46*sa* containing the heartbeat component and the body movement component of the living body 10 and generates a digital signal 46*sb* containing the respiratory component of the living body 10.

(Signal Processing Performed by Digital Signal Generating Unit 40*b*)

Figure 5:
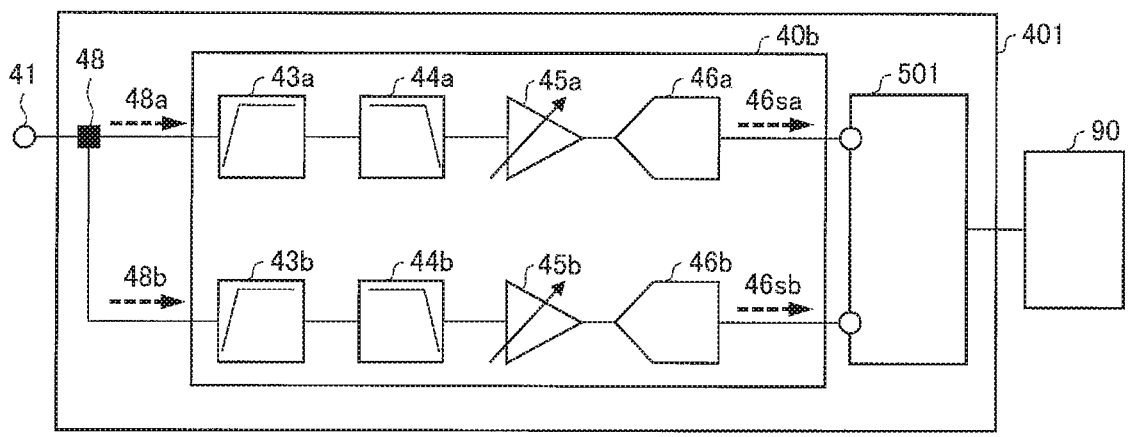
FIG. 5 is a block diagram schematically illustrating the configuration of a signal processing circuit included in a high-frequency device according to the second embodiment of the present invention.

As illustrated in FIG. 5, the digital signal generating unit 40*b* includes the input terminal 41, high-pass filters 43*a* and 43*b*, low-pass filters 44*a* and 44*b*, amplifiers 45*a* and 45*b*, and AD converters 46*a* and 46*b*.

As illustrated in FIG. 5, after having been input to the input terminal 41, at a terminal 48, the analog signal 33*s* is split into two signals: a first analog signal 48*a* and a second analog signal 48*b*.

The first analog signal 48*a* is then limited to a band of heartbeat and body movement and is amplified. As an example, the passband cutoff of the high-pass filter 43*a* is 0.75 Hz, and the passband cutoff of the low-pass filter 44*a* is 10 Hz. An analog signal in a frequency band related to heartbeat and body movement is caused to pass through the high-pass filter 43*a* and the low-pass filter 44*a* and is then amplified by the amplifier 45*a*. The band is limited by the high-pass filter 43*a* in the above manner so as to suppress the respiratory component as much as possible as in the first embodiment.

An analog signal (not illustrated) output from the amplifier 45*a* is input to the AD converter 46*a* and is subjected to analog-to-digital conversion. The first biological digital signal 46*sa* related to the heartbeat component and the body movement component, which has been generated by the AD converter 46*a* performing analog-to-digital conversion, is input to the DSP 501.

In a case of an adult, typically, the surface of the chest part moves by 4 mm to 12 mm during respiration, and the surface of the chest part moves by approximately 0.5 mm during beating of the heart. Thus, the analog signal related to heartbeat is more minute than the analog signal related to respiration. In this respect, by limiting the band by the high-pass filter 43*a* and the low-pass filter 44*a*, it is possible to prevent the amplifier 45*a* from being saturated by the movement of the surface of the chest part during respiration, and it is possible for the AD converter 46*a* to perform analog-to-digital conversion only on the heartbeat component. Accordingly, the dynamic range of the amplitude of the heartbeat waveform over time can be increased, and the sensitivity and accuracy of digital signal processing performed by the DSP 501 can be increased. As an example, only the analog signal containing the heartbeat component and the body movement component with small amplitudes can be subjected to analog-to-digital conversion at 16 bits, and the effects are exhibited particularly during rest or sleeping when the body movement component is small.

On the other hand, the second analog signal 48*b* is limited to a band of respiration and is amplified. As an example, the passband cutoff of the high-pass filter 43*b* is 0.1 Hz, and the passband cutoff of the low-pass filter 44*b* is 0.75 Hz. A signal in a frequency band related to the respiratory component is caused to pass through the high-pass filter 43*b* and the low-pass filter 44*b* and is then amplified by the amplifier 45*b*.

An analog signal (not illustrated) output from the amplifier 45*b* is input to the AD converter 46*b* and is subjected to analog-to-digital conversion. The second biological digital signal 46sb related to the respiratory component, which has been generated by the AD converter 46b performing analog-to-digital conversion, is input to the DSP 501.

The high-pass filter 43b suppresses the dc component, and the low-pass filter 44b suppresses the heartbeat component and the body movement component. Then, by increasing the dynamic range of the respiratory component signal obtained from the second analog signal 48b by the amplifier 45b and the AD converter 46b, the sensitivity and accuracy of digital signal processing performed by the DSP 501 can be increased. As an example, only the analog signal containing the respiratory component can be subjected to analog-to-digital conversion at 16 bits, and the effects are exhibited when the amplitude of the body movement component is large or when the body is moving before sleeping even lying in bed.

(Signal Processing Performed by DSP 501)

As illustrated in FIG. 6, the first biological digital signal 46sa (see FIG. 5) is input to the input terminal 51, and the second biological digital signal 46sb (see FIG. 5) is input to an input terminal 61.

The first biological digital signal 46sa that has been input to the input terminal 51 is split into a heartbeat digital signal 59a related to the heartbeat component and a body movement digital signal 59b related to the body movement component, and the two signals are processed concurrently. In this processing, signal processing for obtaining the number-of-beats-of-heart signal 55s and the heartbeat waveform signal 71a on the basis of the heartbeat digital signal 59a is the same as that in the first embodiment, and therefore description thereof is omitted.

In addition, the second biological digital signal 46sb that has been input to the input terminal 61 is processed without modification as a respiratory digital signal 59c. Signal processing for obtaining the number-of-respirations signal 65s and a respiratory waveform signal 71c2 on the basis of the respiratory digital signal 59c is the same as that in the first embodiment, and therefore description thereof is omitted.

On the other hand, since the movement of the chest part of the living body 10 related to the respiratory component is added as the body movement component, a split signal 71c1 of the respiratory signal extracted by the respiratory signal extracting unit 63 is added to the body movement digital signal 59b. Then, the body movement digital signal 59b is output from the DSP 501 as the body movement waveform signal 71b widely expressing slow body movement and fast body movement.

<Effects>

As described above, according to this embodiment, the digital signal generating unit 40b can increase the dynamic range of each of the first biological digital signal 46sa and the second biological digital signal 46sb. Accordingly, the heartbeat signal extracting unit 53 and the respiratory signal extracting unit 63 can extract the heartbeat signal and the respiratory signal with high sensitivity and accuracy.

Specifically, for example, even while the living body is sleeping in which the amplitude of the body movement component is small (i.e., when the influence of the respiratory component is large), by the digital signal generating unit 40b suppressing the respiratory component of the first analog signal 48a, it is possible to generate the first biological digital signal 46sa with an increased dynamic range. In addition, for example, even while the living body is moving in which the amplitude of the body movement component is large (i.e., when the influence of the body movement component is large), by the digital signal generating unit 40b suppressing the body movement component of the second analog signal 48b, it is possible to generate the second biological digital signal 46sb with an increased dynamic range.

<Modifications>

Note that the digital signal generating unit 40b generates the first biological digital signal 46sa related to the heartbeat component and the body movement component and the second biological digital signal 46sb related to the respiratory component in this embodiment. However, the signals generated by the digital signal generating unit 40b are not limited to those in the above case. For example, the digital signal generating unit 40b may generate three digital signals: a digital signal related to the heartbeat component and the body movement component having a speed equal to the speed of the heartbeat component, a digital signal related to the body movement component having a speed higher than the speed of the heartbeat component, and a respiratory component signal. In addition, four or more digital signals may be generated.

In addition, as in the first embodiment, the DSP 501 and the display 90 may be integrated together. For example, by wirelessly transmitting a signal that has been subjected to analog-to-digital conversion performed by the digital signal generating unit 40b and receiving the signal by a personal computer or the like including the DSP 501 and the display 90, the personal computer or the like may process and display the signal.

Third Embodiment

Another embodiment of the present invention will be described below with reference to FIGS. 7 to 10. Note that the members having the same functions as the members described in the above embodiments are denoted by the same reference numerals, and description thereof is omitted for brevity of the description.

A high-frequency device 3 according to this embodiment is different from the high-frequency devices 1 and 2 according to the first and second embodiments in including a radio wave radar unit 5b instead of the radio wave radar unit 5a and a signal processing circuit 402 instead of the signal processing circuits 400 and 401.

<Signal Processing Performed by Radio Wave Radar Unit 5b>

Now, signal processing performed by the radio wave radar unit 5b will be described below with reference to FIG. 7. FIG. 7 is a block diagram schematically illustrating the configuration of the radio wave radar unit 5b. As illustrated in FIG. 7, the radio wave radar unit 5b includes the oscillator 21, the amplifier 22, the transmission antenna 25, the reception antenna 30, the low-noise amplifier 31, an I mixer 32i, a Q mixer 32q, a filter 33i, a filter 33q, and a phase shifter 38.

As illustrated in FIG. 7, the signal processing from when the transmission signal 11 is emitted from the transmission antenna 25 to when the reflection signal 12 is input to the reception antenna 30 is the same as that in the first and second embodiments. Also, as in the first and second embodiments, the reflection signal 12 includes both a direct reflection signal and an indirect reflection signal.

The signal input to the reception antenna 30 is amplified by the low-noise amplifier 31 and is then split into two signals: an I analog signal 31is and a Q analog signal 31qs. Upon input of the I analog signal 31is to the phase shifter 38, the phase of the I analog signal 31is shifts 90 degrees with respect to that of the Q analog signal 31qs. Then, the I analog signal 31*is* output from the phase shifter 38 is input to the I mixer 32*i*, and the Q analog signal 31*iq* is input to the Q mixer 32*q*.

On the other hand, after having been amplified by the amplifier 22, the analog signal 22*s*, which is one of two signals obtained by splitting a signal, is further split into two signals: an I local oscillation signal 22*is* and a Q local oscillation signal 22*qs*, which are respectively input to the I mixer 32*i* and the Q mixer 32*q*. Note that although the I analog signal 31*is* and the Q analog signal 31*iq* have phases shifted 90 degrees in this embodiment, the I local oscillation signal 22*is* and the Q local oscillation signal 22*qs* may have phases shifted 90 degrees.

The I analog signal 31*is* output from the phase shifter 38 and the Q analog signal 31*iq* are subjected to frequency down conversion performed by the I mixer 32*i* and the Q mixer 32*q*, respectively, and are then input to the filter 33*i* and the filter 33*q*. Then, an I baseband signal 33*is* and a Q baseband signal 33*qs* are output from the filter 33*i* and the filter 33*q*, respectively. Note that the I baseband signal 33*is* is a cosine wave, and the Q baseband signal 33*qs* is a sine wave.

The I baseband signal 33*is* and the Q baseband signal 33*qs* are each an analog signal that has received a Doppler shift due to chest movement including beating of the heart and respiration. Although the difference between the I baseband signal 33*is* and the Q baseband signal 33*qs* is whether or not the signal has passed through the phase shifter 38, since the velocity of signals input to the reception antenna 30 changes over time, both signals have phases shifted 90 degrees at an instant. Accordingly, depending on the magnitude and direction of the signal velocity, the phase relationship between the I baseband signal 33*is* and the Q baseband signal 33*qs* as integral signals output from the radio wave radar unit 5*b* continuously changes over time.

The autocorrelation functions are calculated from each of two channels for I system and for Q system in the above manner because, if the living body 10 slightly moves, the amplitude values of the I baseband signal 33*is* and the Q baseband signal 33*qs* easily change with respect to time. Accordingly, for example, the Q baseband signal 33*qs* may be a more minute signal than the I baseband signal 33*is*. Therefore, the detection of the peak value by using the autocorrelation function of either channel alone may degrade the detection sensitivity and detection accuracy of the peak value.

<Signal Processing Performed by Signal Processing Circuit 402>

Figure 8:
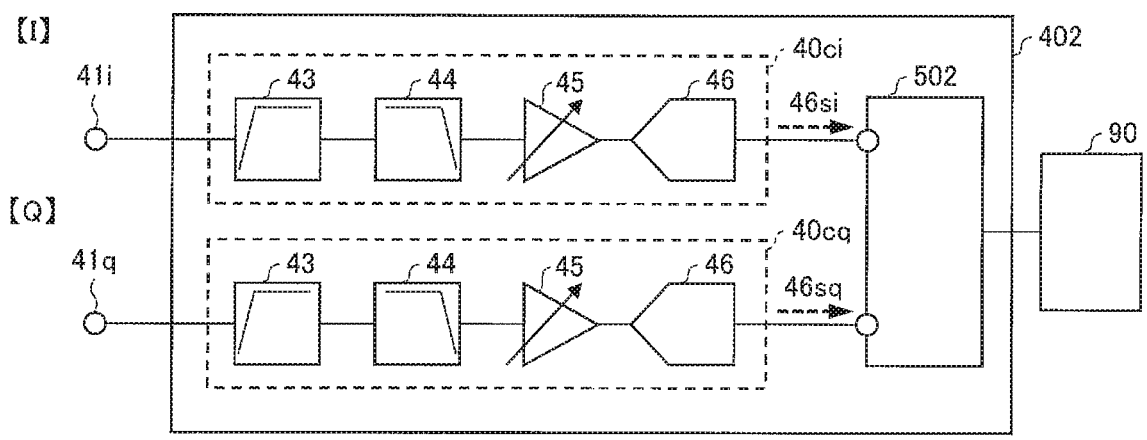
FIG. 8 is a block diagram schematically illustrating the configuration of a signal processing circuit included in the high-frequency device according to the third embodiment of the present invention.

Now, signal processing performed by the signal processing circuit 402 will be described below with reference to FIGS. 8 and 9. FIG. 8 is a block diagram schematically illustrating the configuration of the signal processing circuit 402. FIG. 9 is a block diagram schematically illustrating the configurations of a DSP 502 and the display 90. As illustrated in FIG. 8, the signal processing circuit 402 includes a first digital signal generating unit (digital signal generating unit) 40*ci*, a second digital signal generating unit (digital signal generating unit) 40*cq*, and the DSP 502.

(Signal Processing Performed by First Digital Signal Generating Unit 40*Ci* and Second Digital Signal Generating Unit 40*cq*)

As illustrated in FIG. 8, the I baseband signal 33*is* (see FIG. 7) is input to an input terminal 41*i*, and the Q baseband signal 33*qs* (see FIG. 7) is input to an input terminal 41*q*. Then, the I baseband signal 33*is* that has been input is processed by the I-system first digital signal generating unit 40*ci*, and the Q baseband signal 33*qs* that has been input is processed by the Q-system second digital signal generating unit 40*cq*. Each of the first and second digital signal generating units 40*ci* and 40*cq* has the same configuration as the digital signal generating unit 40*a* (see FIG. 3) for I system and Q system, and therefore description of signal processing performed by the first and second digital signal generating units 40*ci* and 40*cq* is omitted.

An I digital signal 46*si* output from the first digital signal generating unit 40*ci* and a Q digital signal 46*sq* output from the second digital signal generating unit 40*cq* are each limited to a frequency band of the body movement component (including the heartbeat component and the respiratory component) and output as an amplified digital signal and are then subjected to signal processing performed by the DSP 502. Note that the I digital signal 46*si* is a cosine wave, and the Q digital signal 46*sq* is a sine wave.

(Signal Processing Performed by DSP 502)

As illustrated in FIG. 9, the DSP 502 includes input terminals 52*i* and 52*q*, a first heartbeat signal extracting unit (heartbeat signal extracting unit) 53*i*, a second heartbeat signal extracting unit (heartbeat signal extracting unit) 53*q*, a first respiratory signal extracting unit (respiratory signal extracting unit) 63*i*, a second respiratory signal extracting unit (respiratory signal extracting unit) 63*q*, a first heartbeat autocorrelation function processing unit (heartbeat autocorrelation function processing unit) 54*i*, a second heartbeat autocorrelation function processing unit (heartbeat autocorrelation function processing unit) 54*q*, a first respiratory autocorrelation function processing unit (respiratory autocorrelation function processing unit) 64*i*, a second respiratory autocorrelation function processing unit (respiratory autocorrelation function processing unit) 64*q*, a number-of-beats-of-heart determining unit 55*a*, and a number-of-respirations determining unit 65*a*.

As illustrated in FIG. 9, the I digital signal 46*si* (see FIG. 8) that has been input to the input terminal 52*i* is split into three signals: a first I digital signal 58*ai*, a second I digital signal 58*bi*, and a third I digital signal 58*ci*.

The flow of signal processing up to the calculation of the periods of autocorrelation functions on the basis of the first I digital signal 58*ai* and the third I digital signal 58*ci* is the same as that in the first and second embodiments, and therefore description thereof is omitted. In addition, the second I digital signal 58*bi* is output without modification as the body movement waveform signal 71*b* representing the change in the amplitude of body movement over time and is a signal to be input to the display 90.

On the other hand, the Q digital signal 46*sq* (see FIG. 8) that has been input to the input terminal 52*q* is split into two signals: a first Q digital signal 58*aq* and a second Q digital signal 58*bq*.

The flow of signal processing up to the calculation of the periods of autocorrelation functions on the basis of the first Q digital signal 58*aq* and the second Q digital signal 58*bq* is the same as that in the first and second embodiments, and therefore description thereof is omitted.

Then, a first number of beats of the heart, which is the number of beats of the heart calculated by a first heartbeat autocorrelation function processing unit 54*i*, and a second number of beats of the heart, which is the number of beats of the heart calculated by a second heartbeat autocorrelation function processing unit 54*q*, are each input to the number-of-beats-of-heart determining unit 55*a* as a signal (not illustrated) representing the corresponding number of beats of the heart. Specifically, the first number of beats of the heart is input to a first number-of-beats-of-heart determining unit 55*i* included in the number-of-beats-of-heart determining unit 55a. The second number of beats of the heart is input to a second number-of-beats-of-heart determining unit 55q also included in the number-of-beats-of-heart determining unit 55a. Note that the method for determining the first number of beats of the heart and the second number of beats of the heart is the same as that performed by the number-of-beats-of-heart determining unit 55 described in the first embodiment, and therefore description thereof is omitted.

While the living body 10 is at rest, the first number of beats of the heart and the second number of beats of the heart are similar numeric values, but if the I-system channel and the Q-system channel are not well balanced, that is, if the body is moving for example, either channel may produce an abnormal numeric value. Accordingly, as a method in which a display number-of-beats-of-heart determining unit 55b included in the number-of-beats-of-heart determining unit 55a determines the number of beats of the heart to be displayed, for example, as long as the error between the first number of beats of the heart and the second number of beats of the heart is lower than a few percent, the average value thereof may be used as the number of beats of the heart. Alternatively, by comparing the first number of beats of the heart and the second number of beats of the heart, a higher value may be used as the number of beats of the heart.

Then, a first number of respirations, which is the number of respirations calculated by the first respiratory autocorrelation function processing unit 64i, and a second number of respirations, which is the number of respirations calculated by the second respiratory autocorrelation function processing unit 64q, are each input to the number-of-respirations determining unit 65a as a signal (not illustrated) representing the corresponding number of respirations. Specifically, the first number of respirations is input to a first number-of-respirations determining unit 65i included in the number-of-respirations determining unit 65a. In addition, the second number of respirations is input to a second number-of-respirations determining unit 65q also included in the number-of-respirations determining unit 65a. Note that the method for determining the first number of respirations and the second number of respirations are the same as that performed by the number-of-respirations determining unit 65 described in the first embodiment, and therefore description thereof is omitted.

In addition, the method in which a display number-of-respirations determining unit 65b included in the number-of-respirations determining unit 65a determines the number of respirations to be displayed is the same as the above method for determining the number of beats of the heart to be displayed, and therefore description thereof is omitted.

<Method for Determining Periodicity Related to Heartbeat Component by Using Autocorrelation Function>

Next, the method for determining the periodicity related to the heartbeat component by using the autocorrelation function will be described with reference to FIGS. 10(a) and (b). FIG. 10(a) is a graph illustrating the relationship between the amplitude values of heartbeat signals and the numbers of samples related to the heartbeat signals sampled by the first heartbeat autocorrelation function processing unit 54i and the second heartbeat autocorrelation function processing unit 54q. FIG. 10(b) is a graph illustrating the relationship between correlation coefficients of autocorrelation functions and the numbers of samples related to the heartbeat signals sampled by the first heartbeat autocorrelation function processing unit 54i and the second heartbeat autocorrelation function processing unit 54q.

Since biological signals such as the heartbeat signal and the respiratory signal can typically be regarded as signals having finite average power, the signals are expressed as x[n]. n is an integer sample number obtained by sampling. At this time, an autocorrelation function $r_{xx}[l]$ is calculated according to Equation (1).

$$r_{xx}[l] = \lim_{N1 \to \infty} \frac{1}{N1} \sum_{n=0}^{N1-1} x[n]x[n-l]. \quad \text{[Math 1]}$$

l: Delay of sample (integer)
N1: Integer

In addition, the autocorrelation function $r_{xx}[l]$ of a periodic signal where the period is L is calculated according to Equation (2).

$$r_{xx}[l] = \frac{1}{L} \sum_{n=0}^{L-1} x[n]x[n-l] \quad \text{[Math 2]}$$

At this time, if the period L is unknown, Equation (2) cannot be calculated without modification. Accordingly, in Equation (1), an integer whose value is sufficiently large with respect to the assumed period is substituted for N1, and calculation is performed by replacing the following expression in the corresponding part in Equation (1).

$$\frac{1}{N1} \sum_{n=0}^{N1-1} x[n]x[n-l] \quad \text{[Math 3]}$$

The calculation result is used as an approximation of the autocorrelation function $r_{xx}[l]$ defined by Equation (2). If x[n] is a periodic function, the correlation coefficient of the autocorrelation function calculated according to Equation (3) has peak values at L, 2L, 3L, 4L, . . . at regular intervals in addition to where l=0. Furthermore, with a positive peak value that is substantially equal to the peak value obtained when l=0, it can be determined that x[n] is a periodic signal, and accordingly, on the basis of the integer L in this case, the period of the periodic signal is estimated.

If the periodicity related to the heartbeat component is determined by using the autocorrelation function calculated by the DSP 502 by using the above method, the following processing is performed.

Here, the vertical axis in the graph of FIG. 10(a) represents the amplitude value, and the vertical axis in the graph of FIG. 10(b) represents the correlation coefficient. In both of the graphs, the horizontal axis represents the number of samples of heartbeat signals. As the amplitude value and the correlation coefficient increase, the correlativity with past signals increases. In addition, on the basis of the number of samples corresponding to the initial peak value (amplitude value and correlation coefficient) other than n=l=0 in Equation (3), the period of the autocorrelation function is calculated.

In the graph of FIG. 10(b), two autocorrelation functions for I system and Q system are illustrated. Both of the two autocorrelation functions have the initial peak of the correlation coefficient when the number of samples on the horizontal axis is L=46. Here, since the sampling frequency is 50 Hz as in the first and second embodiments, it takes 20 ms for each sample. In addition, since N1=128 times of sampling indicated in Equation (3) is performed in this embodiment, the total sampling time is 20 ms×128=2.56 seconds.

Accordingly, the period T of each of the two autocorrelation functions is 46×20 ms=0.92 seconds. The period T corresponds to 1.087 Hz if converted into the frequency of the heartbeat signal and 65 bpm if converted into the number of beats of the heart per minute.

Note that the periodicity of the two respiratory signals for I system and Q system is similarly determined from the peak values of the two correlation coefficients by using two autocorrelation functions for I system and Q system. Note that since respiration typically occurs once in about four seconds, about 512 times of sampling of respiratory signals is necessary, which differs from the case of the heartbeat signals.

<Effects>

As described above, according to this embodiment, the high-frequency device 3 determines the number of beats of the heart to be finally displayed on the display 90 by using the first number of beats of the heart and the second number of beats of the heart. For example, as long as the error between the first number of beats of the heart and the second number of beats of the heart is lower than a few percent, the number of beats of the heart can be determined by regarding the living body 10 as being static (i.e., the living body 10 is in a state suitable for calculating the number of beats of the heart). The same method can be employed for determining the number of respirations. Accordingly, the high-frequency device 3 can finally display the number of beats of the heart and the number of respirations on the display 90 with high accuracy.

In addition, the high-frequency device 3 determines the first number of beats of the heart and the second number of beats of the heart on the basis of two digital signals (the I digital signal 46$si$ and the Q digital signal 46$sq$) having phases different from each other by 90 degrees. Here, even if the I digital signal 46$si$, which is a cosine wave, is a signal with a small amplitude, being a sine wave, the Q digital signal 46$sq$ is a signal with a large amplitude, and both signals have such a relationship as to complement each other upon changes in phases. Accordingly, even if the living body 10 moves relatively largely, at least one of the numbers of beats of the heart maintains high accuracy. The same applies to the relationship between the first number of respirations and the second number of respirations. Thus, even if the living body 10 moves relatively largely, the high-frequency device 3 can calculate the number of beats of the heart and the number of respirations with high accuracy.

Figure 10:
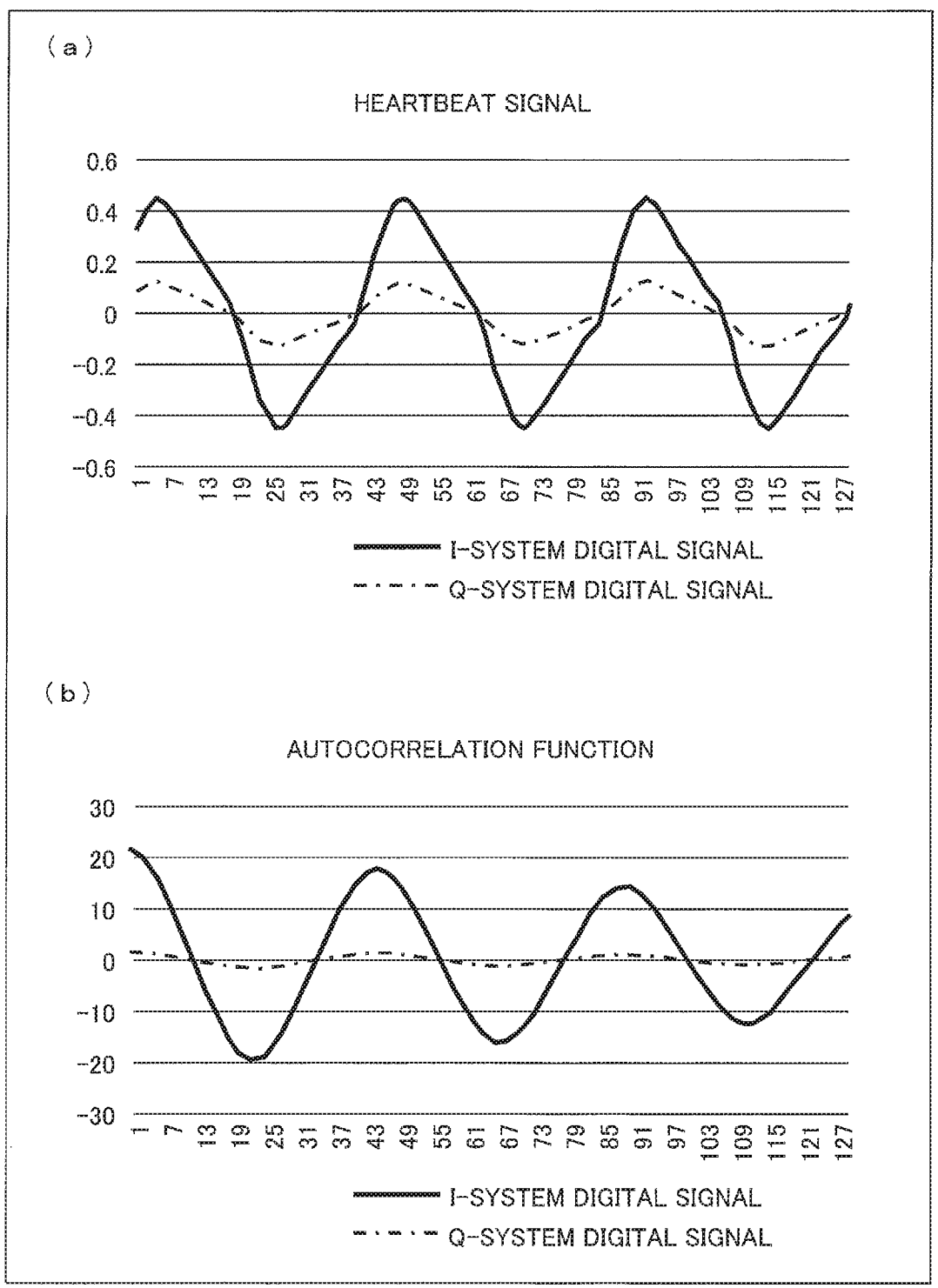
FIG. 10(a) is a graph illustrating the relationship between the amplitude values of heartbeat signals and the numbers of samples related to the heartbeat signals sampled by a first heartbeat autocorrelation function processing unit and a second heartbeat autocorrelation function processing unit included in the high-frequency device.
FIG. 10(b) is a graph illustrating the relationship between correlation coefficients of autocorrelation functions and the numbers of samples related to the heartbeat signals.
Figure 13:
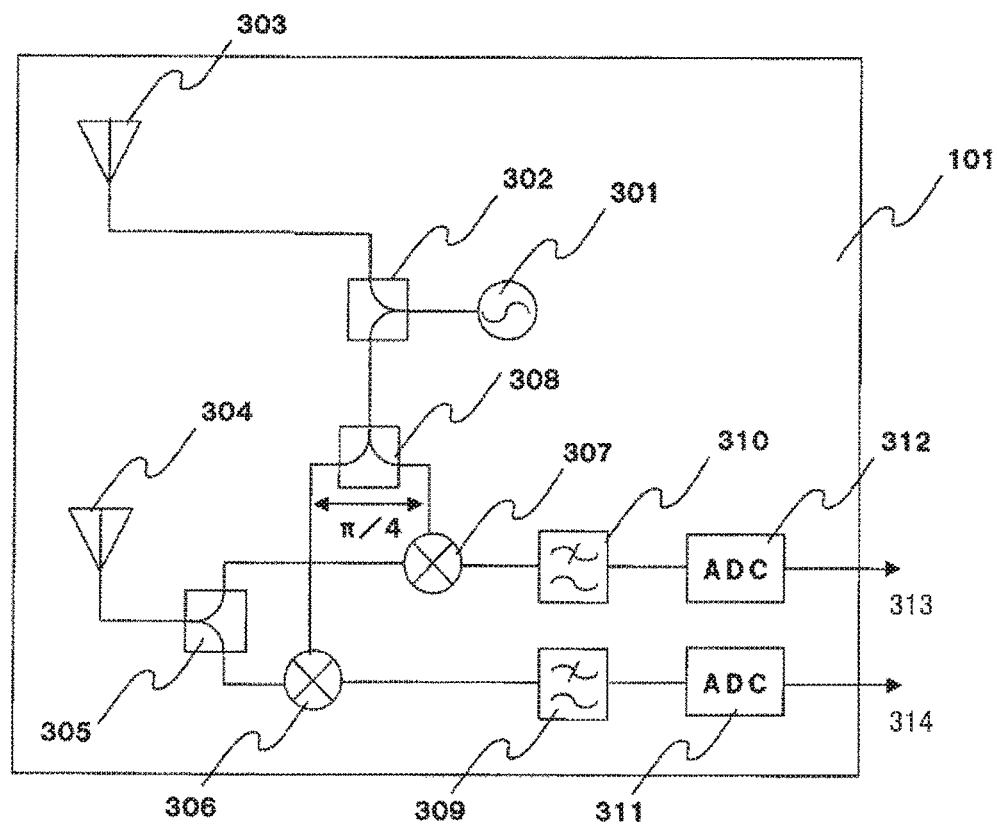
FIG. 13 is a block diagram schematically illustrating the configuration of a sensor unit included in a microwave sensor device of the related art.

Specifically, as illustrated in FIG. 10($a$), the level of the sampled heartbeat signal for I system is different from the level of the sampled heartbeat signal for Q system (the heartbeat signal for Q system has a lower signal level than the heartbeat signal for I system). Accordingly, when determining the periodicity of the heartbeat component and the respiratory component only by using the autocorrelation function of the heartbeat signal for Q system, for example, the accuracy of the determination is decreased. However, by using both the heartbeat signal for I system and the heartbeat signal for Q system as in this embodiment, even a heartbeat signal at a high level can be extracted, and accordingly, the periodicity can be determined by using the autocorrelation functions for both I system and Q system. As a result, it is possible to increase the accuracy for determining the periodicity by the high-frequency device 3. As an example, in FIG. 10($b$), the periodicity obtained by using the autocorrelation function has a peak value L=46 of both the heartbeat signal for I system and the heartbeat signal for Q system, and a number of beats of the heart per minute being 65 bpm is obtained for both signals.

Fourth Embodiment

Another embodiment of the present invention will be described below with reference to FIGS. 11 and 12. Note that the members having the same functions as the members described in the above embodiments are denoted by the same reference numerals, and description thereof is omitted for brevity of the description.

A high-frequency device 4 according to this embodiment is different from the high-frequency devices 1 to 3 according to the first to third embodiments in including a signal processing circuit 403 instead of the signal processing circuits 400 to 402.

<Signal Processing Performed by Signal Processing Circuit 403>

Now, signal processing performed by the signal processing circuit 403 will be described below with reference to FIGS. 11 and 12. FIG. 11 is a block diagram schematically illustrating the configuration of the signal processing circuit 403. FIG. 12 is a block diagram schematically illustrating the configurations of a DSP 503 and the display 90. As illustrated in FIG. 11, the signal processing circuit 403 includes an I heartbeat digital signal generating unit 49$a$, an I respiratory digital signal generating unit 49$b$, a Q heartbeat digital signal generating unit 49$c$, a Q respiratory digital signal generating unit 49$d$, and the DSP 503.

(Signal Processing Performed by Each of Digital Signal Generating Units 49$a$ to 49$d$)

As illustrated in FIG. 11, the I baseband signal 33$is$ (see FIG. 7) is input to an input terminal 41$b$, and the Q baseband signal 33$qs$ (see FIG. 7) is input to an input terminal 41$c$. Then, the I baseband signal 33$is$ that has been input is split into two signals: an I heartbeat analog signal 48$ia$ and an I respiratory analog signal 48$ib$ for I system. In addition, the Q baseband signal 33$qs$ that has been input is split into two signals: a Q heartbeat analog signal 48$qa$ and a Q respiratory analog signal 48$qb$ for Q system.

Here, the I heartbeat analog signal 48$ia$ and the Q heartbeat analog signal 48$qa$ are each an analog signal containing the heartbeat component and the body movement component, and the I respiratory analog signal 48$ib$ and the Q respiratory analog signal 48$qb$ are each an analog signal containing the respiratory component.

Then, the I heartbeat analog signal 48$ia$ is processed by the I heartbeat digital signal generating unit 49$a$, and the I respiratory analog signal 48$ib$ is processed by the I respiratory digital signal generating unit 49$b$. In addition, the Q heartbeat analog signal 48$qa$ is processed by the Q heartbeat digital signal generating unit 49$c$, and the Q respiratory analog signal 48$qb$ is processed by the Q respiratory digital signal generating unit 49$d$. Each of the digital signal generating units 49$a$ to 49$d$ has the same configuration as the digital signal generating unit 40$a$ (see FIG. 3) for I system and Q system, and therefore description of signal processing performed by each of the digital signal generating units 49$a$ to 49$d$ is omitted.

An I heartbeat digital signal 46$sia$ output from the I heartbeat digital signal generating unit 49$a$ and an I respiratory digital signal 46$sib$ output from the I respiratory digital signal generating unit 49$b$ are each processed by the DSP 503. In addition, a Q heartbeat digital signal 46$sqa$ output from the Q heartbeat digital signal generating unit 49$c$ and a Q respiratory digital signal 46$sqb$ output from the Q respiratory digital signal generating unit 49d are each processed by the DSP 503. Note that the digital signals 46sia and 46sib for I system are cosine waves, and the digital signals 46sqa and 46sqb for Q system are sine waves.
(Signal Processing Performed by DSP 503)

As illustrated in FIG. 12, the I heartbeat digital signal 46sia is input to the input terminal 52i. Then, after having been output from the input terminal 52i, the I heartbeat digital signal 46sia is split into two signals: the first I digital signal 58ai and the second I digital signal 58bi. Then, the first I digital signal 58ai is input to a first heartbeat signal extracting unit 53i. In addition, the second I digital signal 58bi is output without modification as the body movement waveform signal 71b representing the change in the amplitude of body movement over time and is a signal to be input to the display 90.

In addition, after having been input to an input terminal 62i, the I respiratory digital signal 46sib is output to the first respiratory signal extracting unit 63i as the third I digital signal 58ci. After having been input to the input terminal 52q, the Q heartbeat digital signal 46sqa is output to the second heartbeat signal extracting unit 53q as the first Q digital signal 58aq. After having been input to an input terminal 62q, the Q respiratory digital signal 46sqb is output to the second respiratory signal extracting unit 63q as the second Q digital signal 58bq.

The flow of signal processing up to the calculation of the period of each autocorrelation function on the basis of the first I digital signal 58ai, the third I digital signal 58ci, the first Q digital signal 58aq, and the second Q digital signal 58bq is the same as that in the first to third embodiments, and therefore description thereof is omitted. In addition, the signal processing for obtaining the heartbeat waveform signal 71a on the basis of the first I digital signal 58ai and the signal processing for obtaining the respiratory waveform signal 71c on the basis of the third I digital signal 58ci are also the same as those in the first to third embodiments, and therefore description thereof is omitted.

Next, the method in which the number-of-beats-of-heart determining unit 55a determines the number of beats of the heart to be displayed and the method in which the number-of-respirations determining unit 65a determines the number of respirations to be displayed are the same as those in the third embodiment, and therefore description thereof is omitted.
<Effects>

As described above, according to this embodiment, the high-frequency device 4 performs analog signal processing and digital signal processing by separating a biological signal (hereinafter referred to as "heartbeat component signal") containing the heartbeat component and the body movement component and a biological signal (hereinafter referred to as "respiratory component signal") containing the respiratory component. Accordingly, the dynamic ranges of the heartbeat component signal and the respiratory component signal can be increased at each stage of the analog signal processing and the digital signal processing. Therefore, each heartbeat autocorrelation function processing unit and each respiratory autocorrelation function processing unit can calculate each number of beats of the heart and each number of respirations with high accuracy.

Specifically, in the heartbeat component signal, it is possible to reduce the influence of the respiratory component, and in the respiratory component signal, it is possible to reduce the influence of the body movement component. The effects of the heartbeat component signal are exhibited during rest and sleeping where body movement is small, whereas the effects of the respiratory component signal are exhibited in a non-static situation where body movement is large and when the body is still moving before sleeping even lying in bed.

In addition, on the basis of each of the numbers of beats of the heart (the first number of beats of the heart and the second number of beats of the heart) and each of the numbers of respirations (the first number of respirations and the second number of respirations), the high-frequency device 4 determines the number of beats of the heart and the number of respirations to be displayed. Accordingly, the high-frequency device 4 can finally display the number of beats of the heart and the number of respirations on the display 90 with high accuracy, and even if the living body 10 moves relatively largely, the high-frequency device 4 can calculate the number of beats of the heart and the number of respirations with high accuracy.
[Examples Realized by Software]

The control block (in particular, the radio wave radar units 5a and 5b and the signal processing circuits 400 to 403) in the high-frequency devices 1 to 4 may be realized by a logic circuit (hardware) formed on an integrated circuit (IC chip) or the like or software by using a central processing unit (CPU).

In the latter case, the high-frequency devices 1 to 4 include a CPU that executes commands of programs, which are software realizing each function, a read only memory (ROM) or a storage device (these are referred to as "recording media") having the programs and various data items recorded thereon in a computer (or CPU)-readable manner, a random access memory (RAM) that loads the programs, and the like. By the computer (or the CPU) reading the programs from the recording media and executing the programs, the object of the present invention is achieved. Examples of each of the recording media include a "non-transitory physical medium" such as a tape, disk, card, semiconductor memory, programmable logic circuit, or the like. In addition, the programs may be supplied to the computer via a given transmission medium (e.g., communication network or broadcast wave) by which the programs can be transmitted. Note that the present invention may also be realized in the form of data signals embedded in a carrier wave embodied by electronic transmission of the programs.
[Conclusion]

A high-frequency device (1, 2, 3, 4) according to a first aspect of the present invention includes a biological signal extracting unit (heartbeat signal extracting unit 53, respiratory signal extracting unit 63) that extracts, from a digital signal representing a biological phenomenon, which is movement that appears in a living body, a biological signal representing a specific frequency component of the digital signal; and an autocorrelation function processing unit (heartbeat autocorrelation function processing unit 54, respiratory autocorrelation function processing unit 64) that samples the biological signal extracted by the biological signal extracting unit, calculates an autocorrelation function on the basis of a predetermined number of the biological signals that are sampled, and determines periodicity of the autocorrelation function from a peak value of a correlation coefficient to calculate biological information representing the biological phenomenon.

In the above configuration, the high frequency device extracts only a necessary band by using an analog filter and causes only the necessary band to pass through a digital filter too. Specifically, by extracting only the necessary band through the analog filter, excluding unnecessary signals, and by amplifying the necessary band, and then by performing analog-to-digital conversion, the high-frequency device increases the dynamic range of the heartbeat or respiration band. In addition, the SN ratio of the digital signal is increased in the digital filter. Accordingly, it is possible to increase the detection accuracy of the peak value of a correlation function detected from the autocorrelation function.

In addition, by detecting the peak value of the correlation coefficient by using the autocorrelation function obtained by sampling biological signals and by determining the period of the autocorrelation function, the high-frequency device calculates the biological information. Accordingly, even if the living body is moving or if there are many noise components such as extraneous reflection signals, the biological information can be calculated with high accuracy.

In a high-frequency device according to a second aspect of the present invention, in the first aspect, the biological signal extracting unit may extract the biological signal from a direct reflection signal (reflection signal 12) and an indirect reflection signal (reflection signal 12), the direct reflection signal being obtained by a transmission signal that has been transmitted from the high-frequency device toward the living body in order to extract the biological signal and that is directly reflected on the living body, the indirect reflection signal being obtained by the transmission signal that has been reflected on an object and then is reflected on the living body.

Typically, since the waveform of an indirect reflection signal is deformed or noise is added thereto, it is considered to be difficult to calculate biological information from the indirect reflection signal.

In this respect, in the above configuration, it is possible to extract a biological signal from the direct reflection signal and the indirect reflection signal by using the biological signal extracting unit. Accordingly, also from the indirect reflection signal, it is possible to calculate the biological information by using the autocorrelation functions of the biological signal.

In addition, if the living body is present in a relatively narrow space such as a bedroom, there are many indirect reflection signals in the space. Accordingly, even if it is not possible to capture the direct reflection signal, the high-frequency device can calculate the biological information of the living body present in the space by using the indirect reflection signals.

Furthermore, if the living body is present in the above space, even in a situation where it is difficult to directly irradiate a desired portion of the living body with the transmission signal, for example, when the living body is lying face down, by making the transmission signal reflect on a wall or the like, the portion can be indirectly irradiated with the transmission signal. Accordingly, by using the indirect reflection signal, it is possible to calculate the biological information regardless of the posture of the living body.

In a high-frequency device according to a third aspect of the present invention, in the first or second aspect, the biological signal extracting unit may include a heartbeat signal extracting unit (53) that extracts a heartbeat signal representing heartbeat at a specific frequency and a respiratory signal extracting unit (63) that extracts a respiratory signal representing respiration at a specific frequency, and the autocorrelation function processing unit may include a heartbeat autocorrelation function processing unit (54) that calculates the number of beats of a heart during a predetermined period and a respiratory autocorrelation function processing unit (64) that calculates the number of respirations during a predetermined period.

According to the above configuration, the high-frequency device can calculate the number of beats of the heart and the number of respirations during a predetermined period by determining the periodicity of autocorrelation functions in the heartbeat signal and the respiratory signal even if the living body is moving or if there are many noise components such as extraneous reflection signals. Accordingly, it is possible to realize a high-frequency device with increased detection sensitivity for calculating the number of beats of the heart and the number of respirations.

A high-frequency device (2) according to a fourth aspect of the present invention may include, in the third aspect, a digital signal generating unit (40b) that generates a first biological digital signal (46sa) related to a heartbeat component and a body movement component and a second biological digital signal (46sb) related to a respiratory component upon an analog signal (first analog signal 48a, second analog signal 48b) related to the biological phenomenon being input, in which the heartbeat signal extracting unit may extract the heartbeat signal on the basis of the first biological digital signal output from the digital signal generating unit, and in which the respiratory signal extracting unit may extract the respiratory signal on the basis of the second biological digital signal output from the digital signal generating unit.

In the above configuration, the digital signal generating unit can increase the dynamic range of each of the first biological digital signal and the second biological digital signal. Accordingly, the heartbeat signal extracting unit and the respiratory signal extracting unit can extract the heartbeat signal and the respiratory signal with high sensitivity and accuracy.

A high-frequency device (3) according to a fifth aspect of the present invention may further include, in the third aspect, a radio wave radar unit (5b) that outputs an I analog signal (31is) related to the biological phenomenon and a Q analog signal (31qs) having a phase 90 degrees different from a phase of the I analog signal; a number-of-beats-of-heart determining unit (55a) that determines the number of beats of the heart; and a number-of-respirations determining unit (65a) that determines the number of respirations, in which the digital signal generating unit (first digital signal generating unit 40ci, second digital signal generating unit 40cq) may generate an I digital signal (46si) related to the heartbeat component, the respiratory component, and the body movement component on the basis of the I analog signal output from the radio wave radar unit and generates a Q digital signal (46sq) related to the heartbeat component, the respiratory component, and the body movement component on the basis of the Q analog signal output from the radio wave radar unit, in which the heartbeat autocorrelation function processing unit (first heartbeat autocorrelation function processing unit 54i, second heartbeat autocorrelation function processing unit 54q) may calculate a first number of beats of the heart during a predetermined period on the basis of the I digital signal and calculates a second number of beats of the heart during a predetermined period on the basis of the Q digital signal, in which the respiratory autocorrelation function processing unit (first respiratory autocorrelation function processing unit 64i, second respiratory autocorrelation function processing unit 64q) may calculate a first number of respirations during a predetermined period on the basis of the I digital signal and calculates a second number of respirations during a predetermined period on the basis of the Q digital signal, in which the number-of-beats-of-heart determining unit may determine the number of beats of the heart on the basis of the first number of beats of the heart and the second number of beats of the heart that have been output from the heartbeat autocorrelation function processing unit, and in which the number-of-respirations determining unit may determine the number of respirations on the basis of the first number of respirations and the second number of respirations that have been output from the respiratory autocorrelation function processing unit.

In the above configuration, the high-frequency device determines the final number of beats of the heart by using the first number of beats of the heart and the second number of beats of the heart. For example, as long as the error between the first number of beats of the heart and the second number of beats of the heart is lower than a few percent, the number of beats of the heart can be determined by regarding the living body as being static (i.e., the living body is in a state suitable for calculating the number of beats of the heart). The same method can be employed for determining the number of respirations. Accordingly, the high-frequency device can finally determine the number of beats of the heart and the number of respirations with high accuracy.

In addition, the high-frequency device determines the first number of beats of the heart and the second number of beats of the heart on the basis of two digital signals (the I digital signal and the Q digital signal) having phases different from each other by 90 degrees. Here, even if the I digital signal, which is a cosine wave, is a signal with a small amplitude, being a sine wave, the Q digital signal is a signal with a large amplitude, and both signals have such a relationship as to complement each other upon changes in phases. Accordingly, even if the living body moves relatively largely, at least one of the numbers of beats of the heart maintains high accuracy. The same applies to the relationship between the first number of respirations and the second number of respirations. Thus, even if the living body moves relatively largely, the high-frequency device can calculate the number of beats of the heart and the number of respirations with high accuracy.

Note that in the high-frequency device (4) according to the fifth aspect, the digital signal generating unit (I heartbeat digital signal generating unit 49a, I respiratory digital signal generating unit 49b, Q heartbeat digital signal generating unit 49c, Q respiratory digital signal generating unit 49d) may generate an I heartbeat digital signal (46sia) related to the heartbeat component and the body movement component and an I respiratory digital signal (46sib) related to the respiratory component on the basis of the I analog signal (I heartbeat analog signal 48ia, I respiratory analog signal 48ib) that has been output from the radio wave radar unit and may generate a Q heartbeat digital signal (46sqa) related to the heartbeat component and the body movement component and a Q respiratory digital signal (46sqb) related to the respiratory component on the basis of the Q analog signal (Q heartbeat analog signal 48qa, Q respiratory analog signal 48qb) that has been output from the radio wave radar unit, the heartbeat autocorrelation function processing unit may calculate the first number of beats of the heart on the basis of the I heartbeat digital signal and may generate the second number of beats of the heart on the basis of the Q heartbeat digital signal, and the respiratory autocorrelation function processing unit may calculate the first number of respirations on the basis of the I respiratory digital signal and may calculate the second number of respirations on the basis of the Q respiratory digital signal.

In the above configuration, the high-frequency device performs analog signal processing and digital signal processing by separating a heartbeat component signal and a respiratory component signal. Accordingly, the dynamic ranges of the heartbeat component signal and the respiratory component signal can be increased at each stage of the analog signal processing and the digital signal processing. Therefore, each heartbeat autocorrelation function processing unit and each respiratory autocorrelation function processing unit can calculate each number of beats of the heart and each number of respirations with high accuracy.

In addition, on the basis of the first number of beats of the heart, the second number of beats of the heart, the first number of respirations, and the second number of respirations, the high-frequency device determines the number of beats of the heart and the number of respirations to be displayed. Accordingly, the high-frequency device can finally determine the number of beats of the heart and the number of respirations with high accuracy, and even if the living body moves relatively largely, the high-frequency device can calculate the number of beats of the heart and the number of respirations with high accuracy.

The high-frequency device (1, 2, 3, 4) according to each embodiment of the present invention may be realized by a computer, in which case a program for controlling the high-frequency device for realizing the high-frequency device by using a computer by causing the computer to operate as each unit (only software component) included in the high-frequency device and a computer-readable recording medium having the program recorded thereon are also included in the scope of the present invention.

The present invention is not limited to each of the above-described embodiments, and various modifications are possible without departing from the scope of the claims. An embodiment obtained by combining technical means as necessary, which are disclosed in different embodiments, is also included in the technical scope of the present invention. In addition, by combining technical means disclosed in the embodiments, a new technical feature can be formed.

INDUSTRIAL APPLICABILITY

A high-frequency device according to the present invention is useful in, for example, detecting a biological signal in a room and detecting a biological signal during a car drive and is applicable to care welfare, medical service, and the like.

REFERENCE SIGNS LIST 1, 2, 3, 4 high-frequency device
5a, 5b radio wave radar unit
10 living body
11 transmission signal
12 reflection signal (direct reflection signal, indirect reflection signal)
31is I analog signal
31qs Q analog signal
40a, 40b digital signal generating unit
40ci first digital signal generating unit (digital signal generating unit)
40cq second digital signal generating unit (digital signal generating unit)
46sa first biological digital signal
46sb second biological digital signal
46si I digital signal
46sq Q digital signal 46*sia* I heartbeat digital signal
46*sib* I respiratory digital signal
46*sqa* Q heartbeat digital signal
46*sqb* Q respiratory digital signal
48*a* first analog signal (analog signal)
48*b* second analog signal (analog signal)
48*ia* I heartbeat analog signal (I analog signal)
48*ib* I respiratory analog signal (I analog signal)
48*qa* Q heartbeat analog signal (Q analog signal)
48*qb* Q respiratory analog signal (Q analog signal)
49*a* I heartbeat digital signal generating unit (digital signal generating unit)
49*b* I respiratory digital signal generating unit (digital signal generating unit)
49*c* Q heartbeat digital signal generating unit (digital signal generating unit)
49*d* Q respiratory digital signal generating unit (digital signal generating unit)
53 heartbeat signal extracting unit
53*i* first heartbeat signal extracting unit (heartbeat signal extracting unit)
53*q* second heartbeat signal extracting unit (heartbeat signal extracting unit)
54 heartbeat autocorrelation function processing unit
54*i* first heartbeat autocorrelation function processing unit (heartbeat autocorrelation function processing unit)
54*q* second heartbeat autocorrelation function processing unit (heartbeat autocorrelation function processing unit)
55, 55*a* number-of-beats-of-heart determining unit
63 respiratory signal extracting unit
63*i* first respiratory signal extracting unit (respiratory signal extracting unit)
63*q* second respiratory signal extracting unit (respiratory signal extracting unit)
64 respiratory autocorrelation function processing unit
64*i* first respiratory autocorrelation function processing unit (respiratory autocorrelation function processing unit)
64*q* second respiratory autocorrelation function processing unit (respiratory autocorrelation function processing unit)
65, 65*a* number-of-respirations determining unit

The invention claimed is:

1. A high-frequency device comprising:
a biological signal extracting processor that extracts, from a digital signal representing a biological phenomenon, a biological signal representing a specific frequency component of the digital signal; and
an autocorrelation function processing circuit that samples the biological signal extracted by the biological signal extracting processor, calculates an autocorrelation function on the basis of a predetermined number of the biological signals that are sampled, and determines periodicity of the autocorrelation function from a peak value of a correlation coefficient to calculate biological information related to the biological phenomenon,
wherein the biological phenomenon is movement that appears in a living body,
wherein the biological signal extracting processor includes a heartbeat signal extracting unit that extracts a heartbeat signal representing heartbeat at a specific frequency and a respiratory signal extracting unit that extracts a respiratory signal representing respiration at a specific frequency,
wherein the autocorrelation function processing circuit includes a heartbeat autocorrelation function processing circuit that calculates the number of beats of a heart during a predetermined period and a respiratory autocorrelation function processing circuit that calculates the number of respirations during a predetermined period,
wherein the high-frequency device further comprises a digital signal generating circuit that generates a first biological digital signal related to a heartbeat component and a body movement component and a second biological digital signal related to a respiratory component upon receiving an analog signal related to the biological phenomenon,
wherein the heartbeat signal extracting unit extracts the heartbeat signal on the basis of the first biological digital signal output from the digital signal generating circuit, and
wherein the respiratory signal extracting unit extracts the respiratory signal on the basis of the second biological digital signal output from the digital signal generating circuit.

2. A high-frequency device that acquires biological information related to a biological phenomenon, which is movement that appears in a living body, by using a reflection signal that is generated from reflection of a transmission signal on the living body, the transmission signal having been transmitted toward the living body, and occurrence of a Doppler shift, comprising:
a biological signal extracting processor that extracts, from a direct reflection signal and an indirect reflection signal, a biological signal representing a specific frequency component of the direct reflection signal or the indirect reflection signal, the direct reflection signal being obtained by the transmission signal having been reflected on the living body, the indirect reflection signal being obtained by the transmission signal that has been directly reflected on an object and then is reflected on the living body; and
an autocorrelation function processing circuit that samples the biological signal extracted by the biological signal extracting processor, calculates an autocorrelation function on the basis of a predetermined number of the biological signals that are sampled, and determines periodicity of the autocorrelation function from a peak value of a correlation coefficient to calculate biological information related to the biological phenomenon
wherein the biological phenomenon is movement that appears in the living body.

3. The high-frequency device according to claim 1, wherein the biological signal extracting processor extracts the biological signal from a direct reflection signal and an indirect reflection signal, the direct reflection signal being obtained by a transmission signal that has been transmitted from the high-frequency device toward the living body in order to extract the biological signal having been directly reflected on the living body, the indirect reflection signal being obtained by the transmission signal that has been reflected on an object and then is reflected on the living body.

4. The high-frequency device according to claim 1, further comprising:
a radio wave radar unit that outputs an I analog signal related to the biological phenomenon and a Q analog signal having a phase 90 degrees different from a phase of the I analog signal;

a number-of-beats-of-heart determining unit that determines the number of beats of a heart; and a number-of-respirations determining unit that determines the number of respirations, wherein the digital signal generating circuit generates an I digital signal related to the heartbeat component, the respiratory component, and the body movement component on the basis of the I analog signal output from the radio wave radar unit and generates a Q digital signal related to the heartbeat component, the respiratory component, and the body movement component on the basis of the Q analog signal output from the radio wave radar unit, wherein the heartbeat autocorrelation function processing circuit calculates a first number of beats of the heart during a predetermined period on the basis of the I digital signal and calculates a second number of beats of the heart during a predetermined period on the basis of the Q digital signal, wherein the respiratory autocorrelation function processing circuit calculates a first number of respirations during a predetermined period on the basis of the I digital signal and calculates a second number of respirations during a predetermined period on the basis of the Q digital signal, wherein the number-of-beats-of-heart determining unit determines the number of beats of the heart on the basis of the first number of beats of the heart and the second number of beats of the heart that have been output from the heartbeat autocorrelation function processing circuit, and wherein the number-of-respirations determining unit determines the number of respirations on the basis of the first number of respirations and the second number of respirations that have been output from the respiratory autocorrelation function processing circuit.

* * * * *